US009157102B2

(12) United States Patent
Miller et al.

(10) Patent No.: US 9,157,102 B2
(45) Date of Patent: Oct. 13, 2015

(54) OVER-EXPRESSION OF NADH-DEPENDENT OXIDOREDUCTASE (*FUCO*) FOR INCREASING FURFURAL OR 5-HYDROXYMETHYLFURFURAL TOLERANCE

(75) Inventors: Elliot N. Miller, Indianapolis, IN (US); Xueli Zhang, Tianjin (CN); Lorraine P. Yomano, Gainesville, FL (US); Xuan Wang, Gainesville, FL (US); Keelnatham T. Shanmugam, Gainesville, FL (US); Lonnie O'Neal Ingram, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 14/008,015

(22) PCT Filed: Mar. 29, 2012

(86) PCT No.: PCT/US2012/031082
§ 371 (c)(1),
(2), (4) Date: Sep. 27, 2013

(87) PCT Pub. No.: WO2012/135420
PCT Pub. Date: Oct. 4, 2012

(65) Prior Publication Data
US 2014/0024086 A1 Jan. 23, 2014

Related U.S. Application Data

(60) Provisional application No. 61/470,642, filed on Apr. 1, 2011.

(51) Int. Cl.
*C12P 7/56* (2006.01)
*C12N 9/04* (2006.01)
*C12P 7/06* (2006.01)
*C12P 7/10* (2006.01)
*C12P 7/46* (2006.01)

(52) U.S. Cl.
CPC ............ *C12P 7/56* (2013.01); *C12N 9/0006* (2013.01); *C12P 7/06* (2013.01); *C12P 7/065* (2013.01); *C12P 7/10* (2013.01); *C12P 7/46* (2013.01); *C12Y 101/01202* (2013.01); *Y02E 50/16* (2013.01); *Y02E 50/17* (2013.01)

(58) Field of Classification Search
None
See application file for complete search history.

(56) References Cited

U.S. PATENT DOCUMENTS

2010/0261239 A1 10/2010 Soucaille et al.

FOREIGN PATENT DOCUMENTS

| WO | WO 2008/116853 | 10/2008 |
| WO | WO 2010/101665 | 1/2010 |
| WO | WO 2010/012604 | * 2/2010 |
| WO | WO 2010/059616 | 5/2010 |

OTHER PUBLICATIONS

Altaras et al., "Enhanced Production of (R)-1,2-Propanediol by Metabolically Engineered *Escherichia coli*", Biotechnol. Prog. 2000, 16, 940-946.*
Almeida, J. R.M., et al., "Metabolic effects of furaldehydes and impacts on biotechnological processes," *Applied Microbiology and Biotechnology*, 2009, vol. 82, pp. 625-638.
Almeida, J. R.M., et al., "NADH-vs NADPH-coupled reduction of 5-hydroxymethyl furfural (HMF) and its implications on product distribution in *Saccharomyces cerevisiae*," *Applied Microbiology and Biotechnology*, 2008, vol. 78, pp. 939-945.
Alvira, P., et al., "Pretreatment technologies for an efficient bioethanol production process based on enzymatic hydrolysis: A review," *Bioresource Technology*, 2010, vol. 101, pp. 4851-4861.
Blikstad, C., et al., "Functional characterization of a stereospecific diol dehydrogenase, FucO, from *Escherichia coli*: Substrate specificity, pH dependence, kinetic isotope effects and influence of solvent viscosity," *Journal of Molecular Catalysis B: Enzymatic*, 2010, vol. 66, pp. 148-155.
Chen, Y.M., et al., "Constitutive activation of the fucAO operon and silencing of the divergently transcribed fucPIK operon by an IS5 element in *Escherichia coli* mutants selected for growth on L-1,2-propanediol," *Journal of Bacteriology*, 1989, vol. 171, No. 11, pp. 6097-6105.
Conway, T., et al., "Similarity of *Escherichia coli* propanediol oxidoreductase (fucO product) and an unusual alcohol dehydrogenase from *Zymomonas mobilis* and *Saccharomyces cerevisiae*," *Journal of Bacteriology*, 1989, vol. 171, No. 7, pp. 3754-3759.
Geddes, C.C., et al., "Optimizing the saccharification of sugar cane bagasse using dilute phosphoric acid followed by fungal cellulases," *Bioresource Technology*, 2010, vol. 101, pp. 1851-1857.
Geddes, C.C., et al., "Simplified process for ethanol production from sugarcane bagasse using hydrolysate-resistant *Escherichia coli* strain MM160," *Bioresource Technology*, 2011, vol. 102, pp. 2702-2711.
Grabar, T.B., et al., "Methylglyoxal bypass identified as source of chiral contamination in L(+) and D(−)-lactate fermentations by recombinant *Escherichia coil*," *Biotechnology Letters*, 2006, vol. 28, pp. 1527-1535.
Jantama, K., et al., "Combining Metabolic Engineering and Metabolic Evolution to Develop Nonrecombinant Strains of *Escherichia coli* C That Produce Succinate and Malate," *Biotechnology and Bioengineering*, Apr. 1, 2008, vol. 99, No. 5, pp. 1140-1153.

(Continued)

*Primary Examiner* — Suzanne M Noakes
(74) *Attorney, Agent, or Firm* — Saliwanchik Lloyd & Eisenschenk

(57) ABSTRACT

The subject invention pertains to the discovery that the NADH-dependent propanediol oxidoreductase (FucO) can reduce furfural. This allows for a new approach to improve furfural tolerance in bacterial and/or yeast cells used to produce desired products. Thus, novel biocatalysts (bacterial, fungal or yeast cells) exhibiting increased tolerance to furfural and 5-hydroxymethylfurfural (5-HMF) are provided as are methods of making and using such biocatalysts for the production of a desired product.

22 Claims, 6 Drawing Sheets

(56) References Cited

OTHER PUBLICATIONS

Jantama, K., et al., "Eliminating Side Products and Increasing Succinate Yields in Engineered Strains of *Escherichia coli* C," *Biotechnology and Bioengineering*, Dec. 1, 2008, vol. 101, No. 5, pp. 881-893.

Jarboe, L.R., et al., "Development of Ethanologenic Bacteria," *Advances in Biochemical Engineering/Biotechnology*, 2007, vol. 108, pp. 237-261.

Jarboe, L.R., et al., "Metabolic Engineering for Production of Biorenewable Fuels and Chemicals: Contributions of Synthetic Biology," *Journal of Biomedicine and Biotechnology*, 2010, Article No. 761042, pp. 1-18.

Laadan, B., et al., "Identification of an NADH-dependent 5-hydroxymethylfurfural-reducing alcohol dehydrogenase in *Saccharomyces cerevisiae*," *Yeast*, 2008, vol. 25, pp. 191-198.

Martinez, A., et al., "Detoxification of Dilute Acid Hydrolysates of Lignocellulose with Lime," *Biotechnology Progress*, 2001, vol. 17, pp. 287-293.

Miller, E.N., et al., "Furfural Inhibits Growth by Limiting Sulfur Assimilation in Ethanologenic *Escherichia coli* Strain LY180," *Applied and Environmental Microbiology*, 2009, vol. 75, No. 19, pp. 6132-6141.

Miller, E.N., et al., "Genetic changes that increase 5-hydroxymethyl furfural resistance in ethanol-producing *Escherichia coli* LY180," *Biotechnology Letters*, 2010, vol. 32, pp. 661-667.

Miller, E.N., et al., "Silencing of NADPH-Dependent Oxidoreductase Genes (*yqhD* and *dkgA*) in Furfural-Resistant Ethanologenic *Escherichia coli*," *Applied and Environmental Microbiology*, 2009, vol. 75, No. 13, pp. 4315-4323.

Reid, M.F., et al., "Molecular Characterization of Microbial Alcohol Dehydrogenases," *Critical Reviews in Microbiology*, 1994, vol. 20, No. 1, pp. 13-56.

Turner, P.C., et al., "YqhC regulates transcription of the adjacent *Escherichia coli* genes *yqhD* and *dkgA* that are involved in furfural tolerance," *Journal of Industrial Microbiology and Biotechnology*, 2011, vol. 38, pp. 431-439.

Wang, X. et al. "Increased Furfural Tolerance Due to Overexpression of NADH-Dependent Oxidoreductase FucO in *Escherichia coli* Strains Engineered for the Production of Ethanol and Lactate" *Applied and Environmental Microbiology*, Aug. 2011, pp. 5132-5140, vol. 77, No. 15.

Written Opinion in International Application No. PCT/US2012/031082, Oct. 30, 2012, pp. 1-5.

Zaldivar, J., et al., "Effect of Alcohol Compounds Found in Hemicellulose Hydrolysate on the Growth and Fermentation of Ethanologenic *Escherichia coli*," *Biotechnology and Bioengineering*, Jun. 5, 2000, vol. 68, No. 5, pp. 524-530.

Zaldivar, J., et al., "Effect of Selected Aldehydes on the Growth and Fermentation of Ethanologenic *Escherichia coli*," *Biotechnology and Bioengineering*, Oct. 5, 1999, vol. 65, No. 1, pp. 24-33.

Zhang, X., et al., "Fermentation of Glycerol to Succinate by Metabolically Engineered Strains of *Escherichia coli*," *Applied and Environmental Microbiology*, 2010, vol. 76, No. 8, pp. 2397-2401.

Zhang, X., et al., "Metabolic evolution of energy-conserving pathways for succinate production in *Escherichia coli*," *Proceedings of the National Academy of Sciences of the United States*, Dec. 1, 2009, vol. 106, No. 48, pp. 20180-20185.

Zhang, X., et al., "Reengineering *Escherichia coli* for Succinate Production in Mineral Salts Medium," *Applied and Environmental Microbiology*, 2009, vol. 75, No. 24, pp. 7807-7813.

\* cited by examiner

OVER-EXPRESSION OF NADH-DEPENDENT OXIDOREDUCTASE (*FUCO*) FOR INCREASING FURFURAL OR 5-HYDROXYMETHYLFURFURAL TOLERANCE

CROSS REFERENCE TO RELATED APPLICATIONS

This application is the U.S. national stage application of International Patent Application No. PCT/US2012/031082, filed Mar. 29, 2012, which claims the benefit of U.S. Provisional Patent Application Ser. No. 61/470,642, filed Apr. 1, 2011, the disclosure of which is hereby incorporated by reference in its entirety, including all figures, tables and nucleic acid sequences.

This invention was made with government support under DE-FG36-080088142 awarded by Department of Energy. The government has certain rights in the invention.

The Sequence Listing for this application is labeled "Seq-List.txt" which was created on Mar. 29, 2012 and is 11 KB. The entire contents of the sequence listing is incorporated herein by reference in its entirety.

BACKGROUND OF THE INVENTION

Carbohydrate components of woody biomass (cellulose and hemicellulose) represent an abundant potential source of sugars for microbial conversion into renewable fuels, plastics, and other chemicals (7, 18, 35). However, cost-effective depolymerization of this complex material to produce fermentable sugar streams remains a major challenge (3, 35). Pretreatment processes such as dilute mineral acids at elevated temperature and pressures open the structure of woody biomass to increase the effectiveness of cellulase enzymes, and hydrolyze the pentose polymers of hemicellulose into monomers. Unwanted side reactions from this pretreatment also produce a mixture of compounds (furans, acetate, soluble products from lignin, and others) that inhibit growth and retard fermentation (1, 18, 31). Most inhibitors can be removed or neutralized by separating the solubilized sugars from the cellulose-enriched fiber using counter-current washing followed by over-liming (25, 26). However, these added process steps would also add cost to renewable products. By developing robust biocatalysts that are resistant to side products from pretreatment it should be possible to design a simpler process (13, 14).

Furfural, the dehydration product of xylose, is of particular importance as a fermentation inhibitor in hemicellulose hydrolysates (1, 31). Furfural concentrations in hemicellulose hydrolysates have been correlated with toxicity (39). The addition of furfural to over-limed hemicellulose hydrolysates has been shown to restore toxicity (25, 26). In model studies with various hydrolysate inhibitors, furfural was unique in potentiating the toxicity of other compounds (39). Furan alcohols (reduced products) are less toxic than the respective aldehydes (38, 39). Several genes encoding oxidoreductases that reduce furfural and 5-hydroxymethylfurfural (5-HMF; dehydration product of hexose sugars) have been implicated in furan tolerance in *Saccharomyces cerevisiae* (2, 20, 22, 23) and in *E. coli* (28-30, 37).

Furfural-resistant mutants of ethanologenic *Escherichia coli* have been isolated and characterized (28, 29, 37). Resistance to low concentrations of furfural was found to result from the silencing of yqhD, an NADPH-dependent, furfural oxidoreductase that is induced by furfural (28, 29, 37). Although there are multiple NADPH-furfural reductases in *E. coli* and conversion of furfural to the less toxic alcohol would be generally regarded as beneficial, the unusually low $K_m$ of YqhD for NADPH appears to compete with biosynthesis for NADPH (29). Metabolic routes for the anaerobic production of NADPH during xylose fermentation are quite limited (12, 16, 34). The metabolism of furfural by YqhD is proposed to inhibit growth and fermentation by depleting the pool of NADPH below that required for essential biosynthetic reactions (28, 29, 37). Sulfate assimilation was identified as a site that is particularly sensitive to NADPH limitation (28). Furan toxicity (furfural and 5-HMF) can be minimized by a variety of approaches that increased the availability of NADPH (FIG. 1) (28-30).

NADH is abundant during fermentation and represents a preferred reductant for furfural conversion to the less toxic alcohol, eliminating any burden on the NADPH pool. Our laboratory previously cloned the *E. coli* fucO gene (11), an NADH-dependent, L-1,2 propanediol reductase that is induced during fucose catabolism (8, 10).

BRIEF SUMMARY OF THE INVENTION

Furfural is an important fermentation inhibitor in hemicellulose sugar syrups derived from woody biomass. The metabolism of furfural by NADPH-dependent oxidoreductases such as YqhD (low $K_m$ for NADPH) is proposed to inhibit the growth and fermentation of xylose in *Escherichia coli* by competing with biosynthesis for NADPH. The discovery that the NADH-dependent propanediol oxidoreductase (FucO) can reduce furfural has provided a new approach to improve furfural tolerance in bacterial, fungal and yeast cells used to produce desired products. Thus, novel biocatalysts (bacterial, fungal and yeast cells) exhibiting increased tolerance to furfural and 5-hydroxymethylfurfural (5-HMF) are provided as are methods of making and using such biocatalysts.

BRIEF DESCRIPTION OF THE DRAWINGS

FIG. 2A. NADPH-dependent reduction of furfural and 5-HMF by cell-free extracts of LY180 containing vector alone (pTrc99A) and IPTG-induced fucO in LY180 (pLOI4319), FIG. 2B. NADH-dependent reduction of furfural and 5-HMF by cell-free extracts of LY180(pTrc99A) and IPTG-induced fucO in LY180(pLOI4319). In FIGS. 2A and 2B, open bars represent activity with furfural (10 mM) as a substrate. Gray bars represent activity with 5-HMF (10 mM). FIG. 2C. In vivo furfural (10 mM) reduction by chloramphenicol-inhibited, non-growing cells (LY180, 0.88 mg cell dry weight ml$^{-1}$) containing vector alone (pTrc99A) or 0.1 mM IPTG-induced fucO in LY180(pLOI4319). FIG. 2D. Growth inhibition of LY180(pTrc99A) with vector alone (Δ, 0 mM IPTG) or pLOI4319 (○, 0 mM IPTG; •, pLOI4319 induced with 0.1 mM IPTG).

and LY180(pLOI4319) were grown for 48 h in tube cultures containing AM1 medium, 15 mM furfural (A and B) or 10 mM furfural (C). IPTG (0.1 mM) was also included with LY180(pLOI4319) to induce fucO. Bars indicate presence (solid) or absence (open) of supplement. FIG. 3A. Yeast extract (1 g liter$^{-1}$). FIG. 3B. Cysteine (0.1 mM). FIG. 3C. AM1-glucose (50 g liter$^{-1}$) replacing xylose.

FIG. 4A. Cell Mass. FIG. 4B. Ethanol. FIG. 4C. Furfural.

FIG. 5A. Cell mass (10 mM furfural). FIG. 5B. D-lactate (10 mM furfural). FIG. 5C. Furfural (10 mM furfural). FIG. 5D. Cell mass (15 mM furfural). FIG. 5E. D-lactate (15 mM furfural). FIG. 5F. Furfural (15 mM furfural).

DETAILED DISCLOSURE OF THE INVENTION

Figure 1:
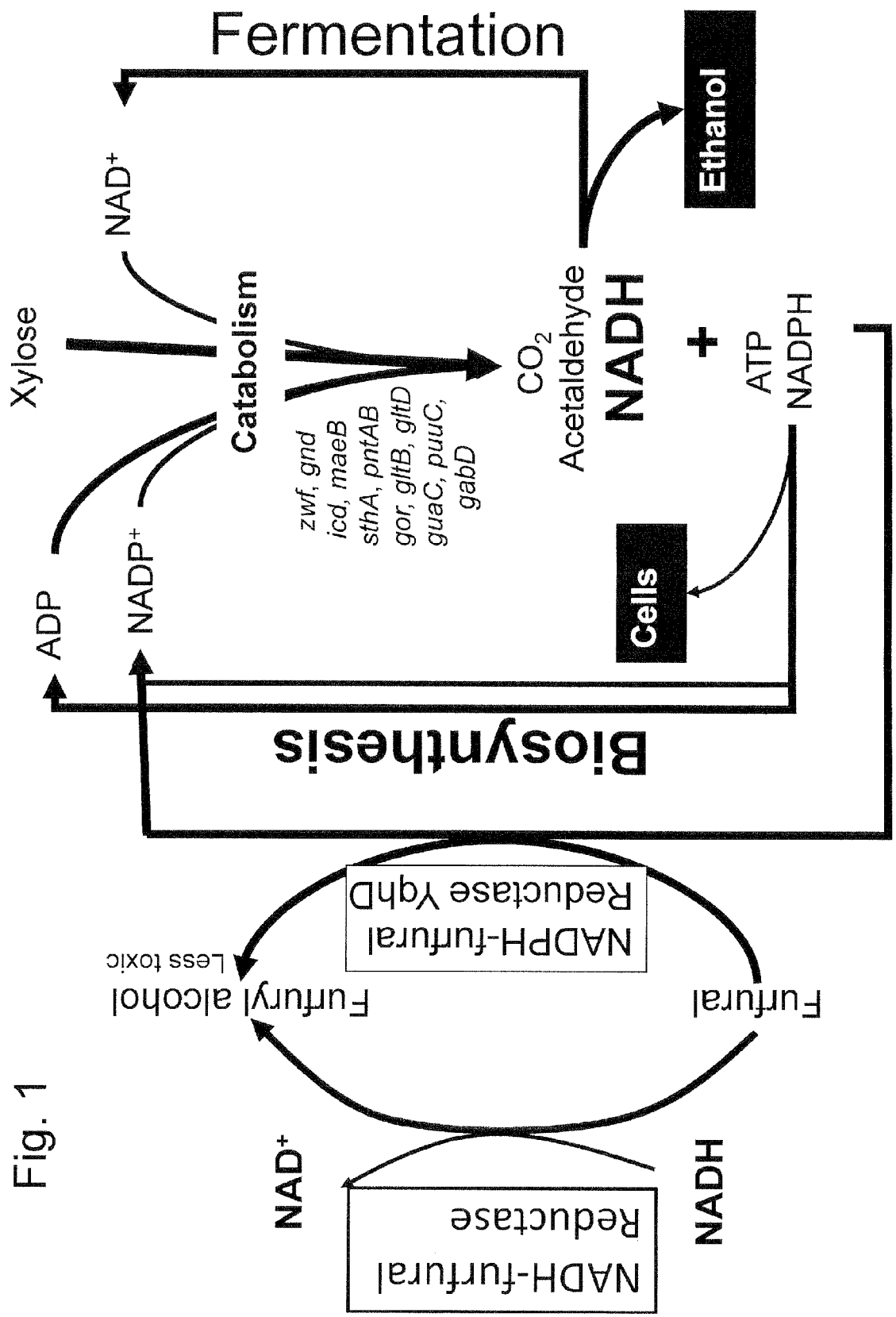
FIG. 1. Role of cofactor metabolism in mediating furfural inhibition of growth. During xylose fermentation, small amounts of NADPH are produced for essential biosynthetic reactions. A partial list of genes encoding activities that could replenish NADPH is also shown. Furfural metabolism by NADPH-dependent oxidoreductases such as YqhD inhibits growth by depleting the NADPH pool (28, 29, 37). NADH-dependent furfural reductases such as FucO can increase furfural tolerance by reducing furfural to the less toxic furfuryl alcohol without depleting the NADPH pool.

The invention provides organisms for production of renewable fuels and other chemicals. Particularly, the invention provides bacteria, fungi and yeast that can grow and produce renewable fuels and other chemicals in the presence of increased furfural. The invention provides for an isolated or recombinant cell (bacterial, yeast or fungal cell) having increased expression of at least one NADH-dependent oxidoreductase (for example, the FucO gene) and that exhibits improved ability to reduce furfural and 5-HMF as compared to a reference cell (e.g., a reference bacterial, yeast or fungal cell). In various embodiments, the bacterial, fungal or yeast cell has increased furfural and 5-HMF tolerance as compared to a reference bacterial, fungal or yeast cell. The bacterial, fungal or yeast cell having increased furfural tolerance may be a wild-type bacterial, fungal or yeast cell that was selected for increased furfural and/or 5-HMF tolerance that is conferred by increased expression or activity of a NADH-dependent oxidoreductase (e.g., FucO). In various embodiments, the bacterial, fungal or yeast cell having increased furfural and/or 5-HMF tolerance can produce ethanol; lactic acid; succinic acid; malic acid; acetic acid; 1,3-propanediol; 2,3-propanediol; pyruvate; dicarboxylic acids; adipic acid; butanol; and amino acids, including aliphatic and aromatic amino acids.

Various publications have disclosed bacterial, fungal or yeast cells in which ethanol; lactic acid; succinic acid; malic acid; acetic acid; 1,3-propanediol; 2,3-propanediol; 1,4-butanediol; 2,3-butanediol; butanol; pyruvate; dicarboxylic acids; adipic acid; and amino acids, including aliphatic and aromatic amino acids can be produced. Many of these microorganisms have been genetically manipulated (genetically engineered) in order to produce these desired products. Exemplary publications in this regard include U.S. Published Patent Applications US-2010/0184171A1 (directed to the production of malic acid and succinic acid), 2009/0148914A1 (directed to the production of acetic acid; 1,3-propanediol; 2,3-propanediol; pyruvate; dicarboxylic acids; adipic acid; and amino acids, including aliphatic and aromatic amino acids), 2007/0037265A1 (directed to the production of chirally pure D and L lactic acid) and PCT application PCT/US2010/029728 (published as WO2010/115067 and directed to the production of succinic acid). The teachings of each of these publications, with respect to the production of bacterial cells producing a desired product, is hereby incorporated by reference in its entirety.

In another aspect of the invention, bacterial, fungal or yeast cells disclosed herein demonstrate increased growth in the presence of furfural and/or 5-HMF as compared to a reference bacterial, fungal or yeast cell. In another embodiment, the bacterial, fungal or yeast cell has increased growth in the presence of furfural and/or 5-HMF at concentrations of about 5 mM, 10 mM, 15 mM, 20 mM, 25 mM, 30 mM, 35 mM, 40 mM or higher (or between about 5 mM and about 20 mM furfural and/or 5-HMF, about 15 mM to about 30 mM furfural and/or 5-HMF, preferably about 15 mM furfural and/or 5 HMF).

Yet other aspects of the invention provide bacterial cells, fungal cells and yeast that demonstrate increased furfural and/or 5-HMF tolerance (have increased FucO activity), as compared to reference bacterial, fungal or yeast cells. Bacterial cells can be selected Gram negative bacteria or Gram positive bacteria. In this aspect of the invention, the Gram-negative bacterial cell can be selected from the group consisting of *Escherichia, Zymomonas, Acinetobacter, Gluconobacter, Geobacter, Shewanella, Salmonella, Enterobacter* and *Klebsiella*. Gram-positive bacteria can be selected from the group consisting of *Bacillus, Clostridium*, Corynebacterial, *Lactobacillus, Lactococcus, Oenococcus, Streptococcus* and Eubacterial cells. Various thermophilic bacterial cells, such as Thermoanaerobes (e.g., *Thermoanaerobacterium saccharolyticum*) can also be manipulated to increase furfural resistance and/or 5-HMF resistance. Other thermophilic microorganisms include, but are not limited to, *Bacillus* spp., e.g., *Bacillus coagulans* strains, *Bacillus licheniformis* strains, *Bacillus subtilis* strains, *Bacillus amyloliquifaciens* strains, *Bacillus megaterium* strains, *Bacillus macerans* strains, *Paenibacillus* spp. strains or *Geobacillus* spp. such as *Geobacillus stearothermophilus* strains can be genetically modified. Other *Bacillus* strain can be obtained from culture collections such as ATCC (American Type Culture Collection) and modified to have increased FucO activity.

Other embodiments provide for a yeast cell or fungal cell having increased FucO activity. The yeast cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

In other embodiments, the cell having increased FucO activity may be a fungal cell. "Fungi" as used herein includes the phyla Ascomycota, Basidiomycota, Chytridiomycota, and Zygomycota, Oomycota and all mitosporic fungi. A fungal cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds., Soc. App. Bacteriol. Symposium Series No. 9, 1980).

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonalum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacteriol. 153: 163; and Hinnen et al., 1978, Proc. Natl. Acad. Sci. USA 75: 1920.

In various embodiments within this aspect of the invention, the bacterial cells can be *Escherichia coli* or *Klebsiella oxytoca*. The invention provides for an isolated or recombinant bacterial cell, wherein FucO activity is increased as compared to a reference bacterial cell. In certain embodiments of this aspect of the invention, bacterial cells can also have YqhD activity decreased or inactivated.

The activity of FucO can be increased in a variety of ways. For example, FucO activity can be increased by expressing the FucO gene in a multicopy plasmid with a native promoter or any other promoter sequence which is known to increase gene expression. Expression of FucO can also be increased by integrating additional copies of the FucO gene within the chromosome of a bacterial cell using transposons. Alternatively, the native promoter of the FucO gene can be replaced by other promoter elements known to enhance the level of gene expression in a bacterial cell. Other techniques for increasing FucO activity, for example mutation of the Fuco improve its kinetic properties or reduce its Km, can also be used to increase the activity of the oxidase. Similar techniques can be used for fungal and yeast cells.

Various other aspects of the invention provide methods of producing ethanol, lactic acid, succinic acid, malic acid, acetic acid, 1,3-propanediol, 2,3-propanediol, 1,4-butanediol, 2,3-butanediol, butanol, pyruvate, dicarboxylic acids, adipic acid or amino acids. In these aspects of the invention, known bacterial, fungal or yeast cells that produce ethanol, lactic acid, succinic acid, malic acid, acetic acid, 1,3-propanediol, 2,3-propanediol, 1,4-butanediol, 2,3-butanediol, pyruvate, dicarboxylic acids, adipic acid or amino acids are manipulated in a manner that results in an increase in FucO activity for the bacterial, fungal or yeast cell (as compared to a reference bacterial, fungal or yeast cell). In various embodiments, the methods comprise culturing a bacterial, fungal or yeast cell producing a desired product (e.g., ethanol, lactic acid, succinic acid, malic acid, acetic acid, 1,3-propanediol, 2,3-propanediol, 1,4-butanediol, 2,3-butanediol, pyruvate, dicarboxylic acids, adipic acid or amino acids) and having increased FucO activity, as compared to a reference cell, under conditions that allow for the production of the desired product. The desired product (e.g., ethanol, lactic acid, succinic acid, malic acid, acetic acid, 1,3-propanediol, 2,3-propanediol, 1,4-butanediol. 2,3-butanediol, pyruvate, dicarboxylic acids, adipic acid or amino acids) can, optionally, be purified from the culture medium in which the bacterial, fungal or yeast cell was cultured. In various other embodiments, the bacterial, fungal or yeast cells can be cultured in the presence of a hemicellulose hydrolysate.

As used herein, "isolated" refers to bacterial, fungal or yeast cells partially or completely free from contamination by other bacteria. An isolated bacterial, fungal or yeast cell (bacterial, fungal or yeast cell) can exist in the presence of a small fraction of other bacteria which do not interfere with the properties and function of the isolated bacterial, fungal or yeast cell (e.g., a bacterial, fungal or yeast cell having increased FucO activity). An isolated bacterial, fungal or yeast cell will generally be at least 30%, 40%, 50%, 60%, 70%, 80%, 85%, 90%, 95%, 98%, or 99% pure. Preferably, an isolated bacterial, fungal or yeast cell according to the invention will be at least 98% or at least 99% pure.

A bacterial, fungal or yeast cell may be a recombinant, non-recombinant or mutant isolated from nature, provided that the bacterial, fungal or yeast cell exhibits higher levels of FucO activity as compared to a reference strain. A non-recombinant bacterial, fungal or yeast cell includes a bacterial, fungal or yeast cell that does not contain heterologous polynucleotide sequences, and is suitable for further modification as disclosed herein, including genetic manipulation for the introduction of heterologous polynucleotide sequences. The term is intended to include progeny of the cell originally transfected. A "recombinant cell" is a bacterial, fungal or yeast cell that contains a heterologous polynucleotide sequence, or that has been treated such that a native polynucleotide sequence has been mutated or deleted. A "mutant" bacterial, fungal or yeast cell is a cell that is not identical to a reference bacterial, fungal or yeast cell, as defined herein below.

A wild-type bacterial, fungal or yeast cell is the typical form of an organism or strain, for example a bacterial cell, as it occurs in nature, in the absence of mutations. Wild-type refers to the most common phenotype in the natural population. "Parental bacterial, fungal or yeast strain", "parental bacterial strain", "parental fungal strain" or "parental yeast strain" is the standard of reference for the genotype and phenotype of a given bacterial, fungal or yeast cell and may be referred to as a "reference strain" or "reference bacterial, fungal or yeast cell". A "parental bacterial, fungal or yeast strain" may have been genetically manipulated or be a "wild-type" bacterial cell depending on the context in which the term is used. Where FucO expression is increased in non-genetically modified bacterial, fungal or yeast cells, the reference strain or reference bacterial, fungal or yeast cell will be a wild-type bacterial, fungal or yeast cell from which the bacterial, fungal or yeast cell having increased FucO activity was obtained as disclosed below.

The terms "increasing", "increase", "increased" or "increases" refers to increasing by at least 5%, for example, 5, 6, 7, 8, 9, 10, 15, 20, 25, 30, 35, 40, 45, 50, 55, 60, 65, 70, 75, 80, 85, 90, 95, 99, 100% or more, a particular activity (e.g., increased FucO activity). The terms "decreasing", "decrease", "decreased" or "decreases" refers to reducing by at least 5%, for example, 5, 6, 7, 8, 9, 10, 15, 20, 25, 30, 35, 40, 45, 50, 55, 60, 65, 70, 75, 80, 85, 90, 95, 99, 100% or more, a particular activity (e.g., decreased FucO activity). An increase (or decrease) in activity includes an increase (or decrease) in the rate and/or the level of a particular activity (e.g., FucO activity). "Growth" means an increase, as defined herein, in the number or mass of a bacterial, fungal or yeast cell over time.

As used herein, "FucO activity" means the reductive removal of furfural and/or 5-HMF by the action of a furfural or 5-HMF NADH-dependent oxidoreductase, such as FucO. The nucleic and amino acid sequence of the FucO gene (SEQ ID NO: 2) and polypeptide (SEQ ID NO: 1) are known in the art (see GenBank Accession Nos. ADT76407.1, for example and GenBank Accession No. CP002185, REGION: 3085103-3086251, VERSION CP002185.1 GI:315059226, Archer et al., BMC Genomics 12 (1), 9 (2011), each of which is hereby incorporated by reference in its entirety) and are provided in the sequence listing appended hereto.

In one aspect of the invention, bacterial cells having increased FucO activity can also have the activity of YqhD, YqhC and/or DkgA protein decreased or altered, as compared to the activity of YqhD, YqhC and/or DkgA protein in a reference bacterial cell or a reference bacterial cell having increased FucO activity. Activity is decreased or altered by methods known in the art, including but not limited to modification of the yqhD, yqhC and/or dkgA gene(s) (e.g. by inserting, substituting or removing nucleic acids or amino acids in the sequences encoding the genes). Thus, this aspect of the invention can also provide a bacterial cell wherein expression of FucO is increased, as compared to a reference bacterial cell and expression of the yqhD, yqhC and/or dkgA gene is/are decreased as compared to the expression of the yqhD, yqhC and/or dkgA gene in a reference bacterial cell. Expression can be decreased or altered by methods known in the art, including but not limited to modification of the yqhD, yqhC and/or dkgA gene(s) (e.g. by inserting, substituting or removing nucleic acids or amino acids in the sequences encoding the genes), inactivation or knockout of these genes. Methods for altering the activity of YqhD, YqhC and/or DkgA and inactivating the genes encoding these proteins are known in the art, see for example PCT/US2010/020051 (PCT publication WO 2010101665 A1) which is hereby incorporated by reference in its entirety.

The invention provides for a bacterial, fungal or yeast cell that has an increased resistance to furfural and further exhibit at least one of: 1) increased growth in the presence or absence of furfural as compared to a reference bacterial, fungal or yeast cell; 2) increased growth and increased production of a desired product as compared to a reference bacterial, fungal or yeast cell; 3) increased growth and increased production of a desired product, in the presence of furfural, as compared to a reference bacterial, fungal or yeast cell; 4) increased growth in the presence of a hydrolysate as compared to a reference bacterial, fungal or yeast cell; and 5) increased production of a desired product as compared to a reference bacterial, fungal or yeast cell.

The invention also provides for a bacterial, fungal or yeast cell that has an increased resistance to 5-HMF and further exhibit at least one of: 1) increased growth in the presence or absence of 5-HMF as compared to a reference bacterial, fungal or yeast cell; 2) increased growth and increased production of a desired product as compared to a reference bacterial, fungal or yeast cell; 3) increased growth and increased production of a desired product, in the presence of 5-HMF, as compared to a reference bacterial, fungal or yeast cell; 4) increased growth in the presence of a hydrolysate as compared to a reference bacterial, fungal or yeast cell; and 5) increased production of a desired product as compared to a reference bacterial, fungal or yeast cell. Methods of increasing the resistance of a bacterial, fungal or yeast cell to furfural and 5-HMF are also provided herein.

Various aspects of the invention provide for the use of a variety of hydrolysates for the production of a desired product, including but not limited to, hydrolysate derived from a biomass, a hemicellulosic biomass, a lignocellulosic biomass or a cellulosic biomass. Yet other aspects of the invention provide a bacterial, fungal or yeast cell with increased resistance to furfural, wherein the bacterial, fungal or yeast cell is capable of producing a desired product as a primary fermentation product, wherein optionally, the primary fermentation product is produced under anaerobic or microaerobic conditions.

As noted above, various aspects of the invention provide for an isolated or recombinant bacterial, fungal or yeast cell, wherein expression of FucO is increased as compared to a reference bacterial, fungal or yeast cell, and wherein the bacterial, fungal or yeast cell has increased furfural tolerance as compared to the reference bacterial, fungal or yeast cell. The invention also provides for an isolated or recombinant bacterial, fungal or yeast cell wherein the expression of FucO or the activity of FucO polypeptides is increased as compared to a reference bacterial, fungal or yeast cell, furfural tolerance is increased in the isolated or recombinant bacterial, fungal or yeast cell, as compared to the reference bacterial, fungal or yeast cell, and wherein the bacterial, fungal or yeast cell is capable of producing a desired product. In this aspect of the invention, the bacterial, fungal or yeast cell can be prepared recombinantly such that FucO activity is increased or by a process comprising the steps of: (a) growing a candidate strain of the bacterial, fungal or yeast cell in the presence of furfural; and (b) selecting bacterial, fungal or yeast cell that produces a desired product in the presence of furfural and has higher FucO activity as compared to a reference bacterial, fungal or yeast cell or parental bacterial, fungal or yeast cell.

The invention also provides for a method for producing a desired product from a biomass, a hemicellulosic biomass, a lignocellulosic biomass, a cellulosic biomass or an oligosaccharide source comprising contacting the biomass, hemicellulosic biomass, lignocellulosic biomass, cellulosic biomass or oligosaccharide with any of the isolated or recombinant bacterial, fungal or yeast cell of the invention thereby producing the desired product from a biomass, hemicellulosic biomass, lignocellulosic biomass, cellulosic biomass or an oligosaccharide source.

Further, the invention provides for a method for producing a desired product from a biomass, a hemicellulosic biomass, a lignocellulosic biomass, a cellulosic biomass or an oligosaccharide source in the presence of furfural comprising contacting the biomass, hemicellulosic biomass, lignocellulosic biomass, cellulosic biomass or oligosaccharide with the isolated or recombinant bacterial, fungal or yeast cell of the invention, thereby producing the desired product from a biomass, hemicellulosic biomass, lignocellulosic biomass, cellulosic biomass or an oligosaccharide source.

The subject application also provides the following non-limiting embodiments:

1. An isolated bacterial, fungal or yeast cell having increased NADH-dependent propanediol oxidoreductase (FucO) activity as compared to a reference bacterial, fungal or yeast cell, wherein said bacterial, fungal or yeast cell having increased FucO activity reduces furfural and/or 5-hydroxymethylfurfural (5-HMF).

2. The isolated bacterial, fungal or yeast cell of embodiment 1, wherein said bacterial, fungal or yeast cell produces a desired product or has been genetically engineered to produce a desired product selected from the group consisting of ethanol, lactic acid, succinic acid, malic acid, acetic acid, 1,3-propanediol, 2,3-propanediol, 1,4-butanediol, 2,3-butanediol, butanol, pyruvate, dicarboxylic acids, adipic acid and amino acids.

3. The isolated bacterial, fungal or yeast cell of embodiments 1-2, wherein said bacterial, fungal or yeast cell exhibits increased production of said desired product as compared to a reference bacterial, fungal or yeast cell in the presence of furfural and/or 5-hydroxymethylfurfural (5-HMF).

4. The isolated bacterial cell of embodiments 1-3, wherein:
    a) expression of the yqhD gene is reduced in said bacterial cell as compared to a reference bacterial cell;
    b) expression of the dkgA gene is reduced in said bacterial cell as compared to a reference bacterial cell;
    c) expression of the yqhD gene, yqhC gene and/or the dkgA gene are reduced in said bacterial cell as compared to expression in a reference bacterial cell;
    d) expression of the yqhC gene is reduced in said bacterial cell as compared to expression in a reference bacterial cell;
    e) expression of the yqhD gene, the yqhC gene and the dkgA genes is reduced in said bacterial cell as compared to expression in a reference bacterial cell;
    f) the yqhD gene is not expressed or is deleted in said bacterial cell;
    g) the yqhD gene and the dkgA gene are not expressed or are deleted in said bacterial cell;
    h) the yqhC gene or yqhD gene, the yqhC gene and the dkgA gene are not expressed or are deleted in said bacterial cell;
    i) the yqhC gene is not expressed or is deleted in said bacterial cell;
    j) expression of the dkgA gene is reduced in said bacterial cell as compared to a reference bacterial cell;
    k) the dkgA gene is not expressed in said bacterial cell;
    l) the activity of the yqhD gene, yqhC gene and/or the dkgA gene product(s) are reduced in said bacterial cell as compared to expression in a reference bacterial cell; or
    m) the activity of the yqhC gene product is reduced in said bacterial cell as compared to expression in a reference bacterial cell.

5. The isolated bacterial cell of embodiment 4, wherein the activity of YqhD protein is reduced in said bacterial cell as compared to a reference bacterial cell.

6. The isolated bacterial cell of embodiment 4, wherein the activity of the YqhD protein and the activity of the DkgA protein is reduced in said bacterial cell as compared to a reference bacterial cell.

7. The isolated bacterial cell of embodiment 4, wherein the activity of the YqhC protein is reduced in said bacterial cell as compared to a reference bacterial cell.

8. The isolated bacterial cell of embodiment 4, wherein regulation of the expression of the yqhD gene is altered to reduce yqhD expression as compared to a reference bacterial cell.

9. The isolated bacterial cell of embodiment 4, wherein regulation of the expression of the yqhD gene and regulation of expression of the dkgA gene is altered to reduce yqhD and dkgA expression in said bacterial cell as compared to expression in a reference bacterial cell.

10. The isolated bacterial cell of embodiment 4, wherein regulation of expression of the yqhC gene is altered to reduce yqhC expression in said bacterial cell as compared to expression in a reference bacterial cell.

11. The isolated bacterial cell of embodiment 4, wherein the yqhC gene, yqhD gene, dkgA gene or any combination thereof is/are deleted in said bacterial cell.

12. The isolated bacterial cell of embodiment 4, wherein there is a change in the activity of the yqhD gene promoter or regulatory protein in said bacterial cell as compared to a reference bacterial cell.

13. The isolated bacterial cell of embodiment 4, wherein there is a change in the activity of the dkgA gene promoter or regulatory protein in said bacterial cell as compared to a reference bacterial cell.

14. The isolated bacterial cell of embodiment 4, wherein the level of YqhD, DkgA and/or YqhC protein is reduced in said bacterial cell due to the addition of an antisense RNA as compared to a reference bacterial cell.

15. The isolated bacterial cell of embodiment 4, wherein the level of YqhD, DkgA and/or YqhC protein is reduced in said bacterial cell due to the addition of an siRNA as compared to a reference bacterial cell.

16. The isolated bacterial, fungal or yeast cell of any preceding embodiment, wherein FucO activity is increased by:
    a) expressing the FucO gene in a plasmid or a multicopy plasmid with a native promoter or a promoter sequence;
    b) transposon integration of additional copies of the FucO gene within the chromosome of a bacterial, fungal or yeast cell;
    c) replacement of the FucO gene native promoter with a promoter that increases the level of gene expression in a bacterial cell; or
    d) the FucO enzyme is mutated to increase catalytic efficiency or reduce its Km.

17. An isolated bacterial, fungal or yeast cell having increased FucO activity wherein said bacterial, fungal or yeast cell is capable of producing a desired product, or which has been genetically engineered to produce a desired product, and wherein said bacterial, fungal or yeast cell is prepared by a process comprising: a) growing a candidate mutant strain of the bacterial, fungal or yeast cell in the presence of furfural or 5-hydroxymethylfurfural (5-HMF); and b) selecting mutants that produce a desired product in the presence of about 5 mM to about 40 mM, about 5 mM to about 20 mM, about 15 to about 30 mM, furfural and/or or 5-hydroxymethylfurfural (5-HMF), preferably about 15 mM furfural or about 15 mM to about 30 mM 5-HMF.

18. The isolated bacterial, fungal or yeast cell of embodiment 17, wherein said cells are grown in the presence of furfural (about 5 mM to about 40 mM, about 5 mM to about 20 mM, about 15 to about 30 mM, about 15 mM or about 15 mM to about 30 mM furfural).

19. The isolated bacterial, fungal or yeast cell of embodiment 17, wherein said cells are grown in the presence of 5-HMF (about 5 mM to about 40 mM, about 5 mM to about 20 mM, about 15 to about 30 mM, about 15 mM or about 15 mM to about 30 mM 5-HMF).

20. The isolated bacterial, fungal or yeast cell of embodiments 17-19, wherein the selected mutants are compared to a reference bacterial, fungal or yeast cell for the ability to produce a desired product in the presence of furfural and/or or 5-hydroxymethylfurfural (5-HMF).

21. A method of growing a bacterial, fungal or yeast cell comprising culturing a bacterial, fungal or yeast cell according to any one of embodiments 1-20 under conditions that allow for the growth of said bacterial, fungal or yeast cell.

22. A method for producing a desired product from a biomass, a hemicellulosic biomass, a lignocellulosic biomass, a cellulosic biomass or an oligosaccharide source comprising contacting the biomass, hemicellulosic biomass, lignocellulosic biomass, cellulosic biomass or oligosaccharide with the isolated bacterial, fungal or yeast cell according to any one of embodiments 1-20 and producing said desired product by fermenting said biomass, a hemicellulosic biomass, a lignocellulosic biomass, a cellulosic biomass or an oligosaccharide source in the presence of said bacterial, fungal or yeast cell.

23. The method of embodiment 21 or 22, wherein the bacterial, fungal or yeast cell produces a desired product, or has been genetically engineered to produce a desired product, selected from the group consisting of ethanol, lactic acid, succinic acid, malic acid, acetic acid, 1,3-propanediol, 2,3-propanediol, 1,4-butanediol, 2,3-butanediol, butanol, pyruvate, dicarboxylic acids, adipic acid and amino acids.

24. The method according to embodiment 21, 22 or 23, wherein said bacterial, fungal or yeast cell exhibits increased production of a desired product as compared to a reference bacterial, fungal or yeast cell in the presence of furfural and/or 5-hydroxymethylfurfural (5-HMF).

25. A method of increasing furfural and/or 5-hydroxymethylfurfural (5-HMF) resistance in a bacterial, fungal or yeast cell comprising increasing NADH-dependent propanediol oxidoreductase (FucO) activity in said bacterial, fungal or yeast cell, as compared to a reference bacterial, fungal or yeast cell, wherein said bacterial, fungal or yeast cell having increased FucO activity reduces furfural and/or 5-hydroxymethylfurfural (5-HMF).

26. The method according to embodiment 25, wherein:
a) expression of the yqhD gene is reduced in said bacterial cell as compared to a reference bacterial cell;
b) expression of the dkgA gene is reduced in said bacterial cell as compared to a reference bacterial cell;
c) expression of the yqhD gene, yqhC gene and/or the dkgA gene are reduced in said bacterial cell as compared to expression in a reference bacterial cell;
d) expression of the yqhC gene is reduced in said bacterial cell as compared to expression in a reference bacterial cell;
e) expression of the yqhD gene, the yqhC gene and the dkgA genes is reduced in said bacterial cell as compared to expression in a reference bacterial cell;
f) the yqhD gene is not expressed or is deleted in said bacterial cell;
g) the yqhD gene and the dkgA gene are not expressed or are deleted in said bacterial cell;
h) the yqhC gene or yqhD gene, the yqhC gene and the dkgA gene are not expressed or are deleted in said bacterial cell;
i) the yqhC gene is not expressed or is deleted in said bacterial cell;
j) expression of the dkgA gene is reduced in said bacterial cell as compared to a reference bacterial cell;
k) the dkgA gene is not expressed in said bacterial cell;
l) the activity of the yqhD gene, yqhC gene and/or the dkgA gene product(s) are reduced in said bacterial cell as compared to expression in a reference bacterial cell; or
m) the activity of the yqhC gene product is reduced in said bacterial cell as compared to expression in a reference bacterial cell.

27. The method according to embodiment 26, wherein the activity of YqhD protein is reduced in said bacterial cell as compared to a reference bacterial cell.

28. The method according to embodiment 26, wherein the activity of the YqhD protein and the activity of the DkgA protein in said bacterial cell is reduced in said bacterial cell as compared to a reference bacterial cell.

29. The method according to embodiment 26, wherein the activity of the YqhC protein is reduced in said bacterial cell as compared to a reference bacterial cell.

30. The method according to embodiment 26, wherein regulation of the expression of the yqhD gene is altered to reduce yqhD expression in said bacterial cell as compared to a reference bacterial cell.

31. The method according to embodiment 26, wherein regulation of the expression of the yqhD gene and regulation of expression of the dkgA gene is altered to reduce yqhD and dkgA expression in said bacterial cell as compared to expression in a reference bacterial cell.

32. The method according to embodiment 26, wherein regulation of expression of the yqhC gene is altered to reduce yqhC expression in said bacterial cell as compared to expression in a reference bacterial cell.

33. The method according to embodiment 26, wherein the yqhC gene, yqhD gene, dkgA gene or any combination thereof is/are deleted.

34. The method according to embodiment 26, wherein there is a change in the activity of the yqhD gene promoter or regulatory protein in said bacterial cell as compared to a reference bacterial cell.

35. The method according to embodiment 26, wherein there is a change in the activity of the dkgA gene promoter or regulatory protein in said bacterial cell as compared to a reference bacterial cell.

36. The method according to embodiment 26, wherein the level of YqhD, DkgA and/or YqhC protein is reduced in said bacterial cell due to the addition of an antisense RNA as compared to a reference bacterial cell.

37. The method according to embodiment 26, wherein the level of YqhD, DkgA and/or YqhC protein is reduced in said bacterial cell due to the addition of an siRNA as compared to a reference bacterial cell.

38. The method according to any one of embodiments 25-37, wherein FucO activity is increased by:

a) expressing the FucO gene in a plasmid or a multicopy plasmid with a native promoter or a promoter sequence;

b) transposon integration of additional copies of the FucO gene within the chromosome of a bacterial, fungal or yeast cell;

c) replacement of the FucO gene native promoter with a promoter that increases the level of gene expression in a bacterial, fungal or yeast cell; or d) the FucO enzyme is mutated to increase catalytic efficiency or reduce its Km.

39. The method according to embodiment 25, wherein said bacterial, fungal or yeast cell is prepared by a process comprising: a) growing a candidate mutant strain of the bacterial, fungal or yeast cell in the presence of furfural or 5-hydroxymethylfurfural (5-HMF); and b) selecting mutants that produce a desired product in the presence of furfural and/or or 5-hydroxymethylfurfural (5-HMF).

40. The method according to embodiment 39, wherein said cell is grown in the presence of furfural.

41. The method according to embodiment 39, wherein said cell is grown in the presence of 5-HMF.

42. The method according to any one of embodiments 39-41, wherein the selected mutants are compared to a reference bacterial, fungal or yeast cell for the ability to produce a desired product in the presence of furfural and/or or 5-hydroxymethylfurfural (5-HMF).

43. The isolated bacterial cell or method according to any one of embodiments 1-42, wherein said bacterial cell is a Gram-negative or a Gram-positive bacterial cell.

44. The isolated bacterial cell or method according to embodiment 43, wherein the Gram-negative bacterial cell is a bacterial cell selected from the genera of *Escherichia, Zymomonas, Acinetobacter, Gluconobacter, Geobacter, Shewanella, Salmonella, Enterobacter* or *Klebsiella* and the Gram-positive bacteria is a bacterial cell selected from the genera of *Bacillus, Clostridium,* Corynebacterial cell, *Lactobacillus, Lactococcus, Oenococcus, Streptococcus* and Eubacterial cell.

45. The isolated bacterial cell or method according to embodiment 44, wherein the bacterial cell is *Escherichia coli* or *Klebsiella oxytoca*.

46. The isolated bacterial cell or method according to embodiment 43, wherein said bacterial cell is selected from *Thermoanaerobes, Bacillus* spp., *Paenibacillus* spp. or *Geobacillus* spp.

47. The isolated yeast cell or method according to any one of embodiments 1-42, wherein said yeast cell is a *Candida, Hansenula, Kluyveromyces, Pichia, Saccharomyces, Schizosaccharomyces,* or *Yarrowia* cell.

48. The isolated yeast cell or method according to embodiment 47, wherein said yeast cell is *Kluyveromyces lactic, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica*.

49. The isolated fungal cell or method according to embodiments 1-42, wherein said fungal cell is a *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Veurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

50. The isolated fungal cell or method according to embodiment 49, wherein said fungal cell is an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

51. The isolated bacterial, fungal or yeast cell according to any one of embodiments 1-20 or 43-50, wherein said bacterial, fungal or yeast cell produce a desired product in the presence of about 5 mM to about 40 mM, about 5 mM to about 20 mM, about 15 mM to about 30 mM, or about 15 mM furfural and/or 5-HMF.

52. An isolated bacterial, fungal or yeast cell having increased NADH-dependent furfural or 5-HMF oxidoreductase activity as compared to a reference bacterial, fungal or yeast cell, wherein said bacterial, fungal or yeast cell having increased NADH-dependent furfural or 5-HMF oxidoreductase activity reduces furfural and/or 5-hydroxymethylfurfural (5-HMF).

53. The isolated bacterial, fungal or yeast cell of embodiment 52, wherein said bacterial cell produces a desired product, or has been genetically engineered to produce a desired product, selected from the group consisting of ethanol, lactic acid, succinic acid, malic acid, acetic acid, 1,3-propanediol, 2,3-propanediol, 1,4-butanediol, 2,3-butanediol, butanol, pyruvate, dicarboxylic acids, adipic acid and amino acids.

54. The isolated bacterial, fungal or yeast cell of embodiments 52-53, wherein said bacterial, fungal or yeast cell exhibits increased production of said desired product as compared to a reference bacterial, fungal or yeast cell in the presence of furfural and/or 5-hydroxymethylfurfural (5-HMF).

55. The isolated bacterial, fungal or yeast cell of embodiments 52, 53 or 54, wherein FucO activity is increased by:

a) expressing one or more NADH-dependent furfural or 5-HMF oxidoreductase in a plasmid or a multicopy plasmid with a native promoter or a promoter sequence;

b) transposon integration of additional copies of a NADH-dependent furfural or 5-HMF oxidoreductase gene within the chromosome of a bacterial, fungal or yeast cell;

c) replacement of a native promoter for a NADH-dependent furfural or 5-HMF oxidoreductase with a promoter that increases the level of gene expression in a bacterial, fungal or yeast cell; or d) a NADH-dependent furfural or 5-HMF oxidoreductase enzyme is mutated to increase catalytic efficiency or reduce its Km.

56. An isolated bacterial, fungal or yeast cell having increased FucO activity wherein said bacterial, fungal or yeast cell is capable of producing a desired product, or has been genetically engineered to produce a desired product, and wherein said bacterial, fungal or yeast cell is prepared by a process comprising: a) growing a candidate mutant strain of the bacterial, fungal or yeast cell in the presence of furfural or 5-hydroxymethylfurfural (5-HMF); and b) selecting mutants that produce a desired product, or has been genetically engineered to produce a desired product and produce said product, in the presence of about 5 mM to about 40 mM, about 5 mM to about 20 mM, about 15 to about 30 mM, furfural and/or or 5-hydroxymethylfurfural (5-HMF), preferably about 15 mM furfural or about 15 mM to about 30 mM 5-HMF.

57. The isolated bacterial, fungal or yeast cell of embodiment 56, wherein said cells are grown in the presence of furfural (about 5 mM to about 40 mM, about 5 mM to about 20 mM, about 15 to about 30 mM, about 15 mM or about 15 mM to about 30 mM furfural).

58. The isolated bacterial, fungal or yeast cell of embodiment 56, wherein said cells are grown in the presence of 5-HMF (about 5 mM to about 40 mM, about 5 mM to about 20 mM, about 15 to about 30 mM, about 15 mM or about 15 mM to about 30 mM 5-HMF).

59. The isolated bacterial, fungal or yeast cell of embodiments 56-58, wherein the selected mutants are compared to a reference bacterial, fungal or yeast cell for the ability to produce a desired product in the presence of furfural and/or or 5-hydroxymethylfurfural (5-HMF).

60. A method of growing a bacterial, fungal or yeast cell comprising culturing a bacterial, fungal or yeast cell according to any one of embodiments 52-59 under conditions that allow for the growth of said bacterial, fungal or yeast cell.

61. A method for producing a desired product from a biomass, a hemicellulosic biomass, a lignocellulosic biomass, a cellulosic biomass or an oligosaccharide source comprising contacting the biomass, hemicellulosic biomass, lignocellulosic biomass, cellulosic biomass or oligosaccharide with the isolated bacterial, fungal or yeast cell according to any one of embodiments 52-59 and producing said desired product by fermenting said biomass, a hemicellulosic biomass, a lignocellulosic biomass, a cellulosic biomass or an oligosaccharide source in the presence of said bacterial, fungal or yeast cell.

62. The method of embodiment 60 or 61, wherein the bacterial, fungal or yeast cell produces a desired product, or has been genetically engineered to produce a desired product, selected from the group consisting of ethanol, lactic acid, succinic acid, malic acid, acetic acid, 1,3-propanediol, 2,3-propanediol, 1,4-butanediol, 2,3-butanediol, butanol, pyruvate, dicarboxylic acids, adipic acid and amino acids.

63. The method according to embodiment 60, 61 or 62, wherein said bacterial, fungal or yeast cell exhibits increased production of a desired product as compared to a reference bacterial, fungal or yeast cell in the presence of furfural and/or hydroxymethylfurfural (5-HMF).

64. A method of increasing furfural and/or 5-hydroxymethylfurfural (5-HMF) resistance in a bacterial, fungal or yeast cell comprising increasing NADH-dependent furfural or 5-HMF oxidoreductase activity in said bacterial, fungal or yeast cell, as compared to a reference bacterial, fungal or yeast cell, wherein said bacterial, fungal or yeast cell having increased FucO activity reduces furfural and/or 5-hydroxymethylfurfural (5-HMF) and produces a desired product, as disclosed herein, or has been genetically engineered to produce a desired product.

65. The isolated bacterial cell or method according to any one of embodiments 52-64, wherein said bacterial cell is a Gram-negative or a Gram-positive bacterial cell.

66. The isolated bacterial cell or method according to embodiment 65, wherein the Gram-negative bacterial cell is a bacterial cell selected from the genera of *Escherichia, Zymomonas, Acinetobacter, Gluconobacter, Geobacter, Shewanella, Salmonella, Enterobacter* or *Klebsiella* and the Gram-positive bacteria is a bacterial cell selected from the genera of *Bacillus, Clostridium*, Corynebacterial cell, *Lactobacillus, Lactococcus, Oenococcus, Streptococcus* and Eubacterial cell.

67. The isolated bacterial cell or method according to embodiment 66, wherein the bacterial cell is *Escherichia coli* or *Klebsiella oxytoca*.

68. The isolated bacterial cell or method according to embodiment 66, wherein said bacterial cell is selected from *Thermoanaerobes, Bacillus* spp., *Paenibacillus* spp. or *Geobacillus* spp.

69. The isolated yeast cell or method according to any one of embodiments 52-64, wherein said yeast cell is a *Candida, Hansenula, Kluyveromyces, Pichia, Saccharomyces, Schizosaccharomyces*, or *Yarrowia* cell.

70. The isolated yeast cell or method according to embodiment 69, wherein said yeast cell is *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica*.

71. The isolated fungal cell or method according to embodiments 52-64, wherein said fungal cell is a *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

72. The isolated fungal cell or method according to embodiment 71, wherein said fungal cell is an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus* eryngii, *Thielavia terrestris, Trametes villosa, Trametes versicolor, Trichoderma harzianum, Trichoderma koningii, Trichoderma longibrachiatum, Trichoderma reesei,* or *Trichoderma viride* cell.

73. The isolated bacterial, fungal or yeast cell or method according to any one of embodiments 52-72, wherein said bacterial, fungal or yeast cell produce a desired product in the presence of about 5 mM to about 40 mM, about 5 mM to about 20 mM, about 15 mM to about 30 mM, or about 15 mM furfural and/or 5-HMF.

74. The method of embodiments 60, 61, 62 or 63, wherein said bacterial, fungal or yeast cell produce a desired product in the presence of about 5 mM to about 40 mM, about 5 mM to about 20 mM, about 15 mM to about 30 mM, or about 15 mM furfural.

75. The method of embodiments 60, 61, 62 or 63, wherein said bacterial, fungal or yeast cell produce a desired product in the presence of about 5 mM to about 40 mM, about 5 mM to about 20 mM, about 15 mM to about 30 mM, or about 15 mM 5-HMF.

76. The isolated bacterial, fungal or yeast cell or method according to any one of the preceding embodiments, wherein said bacterial, fungal or yeast cell has been genetically engineered to produce a desired product, selected from the group consisting of ethanol, lactic acid, succinic acid, malic acid, acetic acid, 1,3-propanediol, 2,3-propanediol, 1,4-butanediol, 2,3-butanediol, butanol, pyruvate, dicarboxylic acids, adipic acid and amino acids.

The terms comprise, comprises, comprising, having and containing are open-ended terms and can be used interchangeably with consisting, consists or consisting essentially of throughout the subject application and claims.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1

Alteration of FucO Activity for the Production of a Desired Product

Strains, Media and Growth Conditions

Strains, plasmids and primers used in this study are listed in Table 1. During strain constructions, cultures were grown aerobically in Luria broth containing 20 g liter$^{-1}$ glucose or 50 g liter$^{-1}$ arabinose. Ampicillin (50 mg liter$^{-1}$), kanamycin (50 mg liter$^{-1}$), or chloramphenicol (40 mg liter$^{-1}$) were added as appropriate. Red recombinase technology (Gene Bridges GmbH, Dresden, Germany) was used to facilitate chromosomal integration as previously described (17, 19, 40, 41). All constructions were verified by DNA sequencing.

Strain LY180 was previously engineered for ethanol production (29). A derivative of LY180 was constructed with a deletion in the yqhD gene (29) encoding a NADPH-dependent furfural reductase activity, now designated strain EM322. Strain EMFR9 is a mutant of LY180 selected for furfural resistance by serial cultivation in AM1-xylose medium containing added furfural (29). This strain was found to contain an IS10 insertion in an adjacent regulatory gene (yqhC) that silenced the expression of yqhD (37).

Strain MM160 is a derivative of strain LY180 selected for resistance to hemicellulose hydrolysates of sugar cane that contains furfural and other inhibitors (13). Partial sequencing of this strain revealed a nonsense mutation, truncating the YqhD protein after the methionine at position 245. Additional genetic modifications were made in strain MM160 to engineer new strains for L- and D-lactate production. The *E. coli* ldhA gene was restored in the chromosome (D-lactate dehydrogenase) as previously described (17, 19). The *Zymomonas mobilis* ethanol pathway (pdc, adhA, and adhB) and the *Pseudomonas putida* esterase gene estZ with an adjacent FRT site were then deleted to produce XW043 for D-lactate production. The native ldhA ORF in XW043 was replaced with *Pediococcus acetolactici* ldhL ORF (L-lactate dehydrogenase) from *E. coli* TG108 (15) to produce strain XW042 for the production of L-lactate.

Lactate strains were grown in small fermentation vessels (500-ml; 300 ml broth) at 37° C. (150 rpm) in AM1 mineral salts medium (24) containing 50 g liter$^{-1}$ xylose or 1 mM betaine and 100 g liter$^{-1}$ xylose. Fermentations were maintained at pH 7.0 (lactate production) by the automatic addition of KOH. Lactate strains were serially transferred for approximately 500 generations to improve xylose utilization and lactate productivity. The resulting strains were designated XW068 (D-lactate) and XW059 (L-lactate).

Furfural Toxicity and Furfural Reduction In Vivo

Furfural toxicity was measured in tube cultures (13 mm by 100 mm) containing 4 ml of AM1 medium with 50 g xylose, 12.5 mg liter$^{-1}$ ampicillin, furfural, and other supplements as indicated (28, 29). Cultures were inoculated to an initial density of 22 mg dew IPTG (0.1 mM) was included for fucO induction. Cell mass was measured at 550 nm after incubation for 48 h (37° C.).

In vivo furfural reduction was measured during incubation in AM1 medium containing 10 mM furfural and 50 g liter$^{-1}$ xylose. Cells were pre-incubated with chloramphenicol (40 mg liter$^{-1}$) for 1 h to arrest growth (0.88 mg dew cells ml$^{-1}$), prior to the addition of furfural. Furfural concentration was measured as previously described using a Beckman spectrophotometer DU800 (27).

Plasmids for fucO Expression

Plasmids were constructed for the controlled expression of fucO. The DNA sequence of fucO (coding region, ribosome binding site, and terminator) were amplified from *E. coli* LY180 by PCR and cloned between the EcoRI and BamHI sites of pTrc99A to produce pLOI4319. This plasmid was used for the inducible expression of fucO. The FucO coding region was cloned into pET15b to produce pLOI4322. This enzyme was purified as a his-tagged product.

FucO Assay and Purification

Cultures were grown overnight to a cell density of approximately 0.66 mg dew ml$^{-1}$ (37° C.) in closed tubes containing 20 ml AM1 (50 g liter$^{-1}$ xylose, 0.1 mM IPTG and 12.5 mg liter$^{-1}$ ampicillin). Cells were harvested by centrifugation (7,000 g for 5 min, 4° C.), washed twice with 10 ml of cold sodium phosphate buffer (50 mM pH 7.0), resuspended to a cell density of 4.4 mg dew ml$^{-1}$, and disrupted in buffer containing 1 mM dithiothreitol using a Fastprep-24 (MP Biomedicals, Solon, Ohio). After clarification at 13,000 g (10 min, 4° C.), protein concentration was determined using a BCA™ Protein Assay Kit (Thermo Scientific, Rockford, Ill.). Furfural-dependent reduction was measured using NADH and NADPH by monitoring the decrease in absorbance at 340 nm (extinction coefficient of NADH of 6,220 M$^{-1}$ cm$^{-1}$; extinction coefficient of NADPH of 6,020 M$^{-1}$ cm$^{-1}$). Reaction mixtures contained 200 mM phosphate buffer (pH 7.0), 10 mM furfural, and 0.2 mM NADH or NADPH. NADH-dependent and NADPH-dependent reduction of 5-HMF (10 mM) was measured in a similar fashion.

For the purification of his-tagged FucO, BL21(pLOI4322) was grown in Luria broth at 37° C. When the culture density reached 0.35 g dew liter$^{-1}$, IPTG (0.1 mM) was added to induce overexpression. After incubation for 4 h, cells were harvested (7,000 g for 5 min, 4° C.), washed once with 10 mM Tris-HCl (pH 7.1), and lysed using a French pressure cell. After clarification at 30,000 g (1 h, 4° C.), crude extracts were passed through a 0.22 µm polyvinylidene fluoride (PVDF) filter, and further purified using a 1-ml HiTrap™ nickel column (GE Healthcare, Piscataway, N.J.). Purified enzyme was dialyzed in 100 mM phosphate buffer using a Thermo Slide-A-Lyzer and quantified using the BCA™ Protein Assay Kit (Thermo Scientific, Rockford, Ill.). A single band was observed in a sodium dodecyl sulfate-polyacrylamide gel.

Effect of fucO Expression on Fermentation

Seed pre-cultures of strains containing pTrc99A or pLOI4319 were grown from plates using sealed culture tubes containing AM1 medium (20 g liter$^{-1}$ xylose, 12.5 mg liter$^{-1}$ ampicillin). MOPS buffer (100 mM; pH 7.0) was included for seed cultures of lactate strains XW068 and XW059. After incubation for 16 h, pre-inocula were diluted into 500-ml fermentation vessels containing 300 ml AM1 media (100 g liter$^{-1}$ xylose, 1 mM betaine, 0.1 mM IPTG, 12.5 µg ml$^{-1}$ ampicillin) to provide a starting density of 13.2 mg dcw. After 24 h growth, these seed cultures were used to provide a starting inoculum for batch fermentations (AM1 medium, 100 g liter$^{-1}$ xylose, 12.5 µg ml$^{-1}$ ampicillin, 0.1 mM IPTG, 13.2 mg dcw initial density, and furfural). Fermentations were maintained at pH 6.5 (ethanol) or pH 7.0 (lactate) by the automatic addition of KOH as previously described (15, 29). Ethanol was measured using an Agilent 6890N gas chromatograph (Palo Alto, Calif.) equipped with flame ionization detectors and a 15-meter HP-Plot Q Megabore column. Furfural concentration was monitored using a Beckman DU spectrophotometer (27, 29). Organic acids and xylose were measured by high-performance liquid chromatography (15).

Results:

FucO has NADH-Dependent Furan Reductase Activity.

The fucO gene was cloned (pLOI4319) and transformed into LY180. Cell lysates were compared to LY180 with vector alone (FIGS. 2A and 2B). Control lysates with vector exhibited low levels of NADPH-dependent furan reductase activity for both furfural and 5-HMF, and even lower levels of NADH-depended activity (FIG. 2B). Expression of fucO from pLOI4319 resulted in a 60-fold increase in NADH-dependent furfural reductase activity and a 6-fold increase in NADH-dependent 5-HMF reductase activity, but no increase in NADPH-dependent activity.

His-tagged fucO was overexpressed in BL21(λDE3) and purified to homogeneity. This protein catalyzed the NADH-specific reduction of furfural and 5-HMF with apparent $K_m$ values of 0.4±0.2 mM and 0.7±0.3 mM, respectively. Apparent $V_{max}$ values for furfural and 5-HMF were 1.9±0.4 and 0.30±0.05 mmol min$^{-1}$ mg protein$^{-1}$, respectively. No NADPH-dependent furfural or 5-HMF reductase activity was observed with the purified enzyme. The apparent $K_m$ value for furfural (0.4 mM) with FucO was significantly lower than that of YqhD (9 mM furfural) (29).

Expression of fucO Increased Furfural Metabolism In Vivo and Increased Furfural Tolerance in Tube Cultures.

IPTG-induced expression of fucO in LY180(pLOI4319) increased the in vivo specific activity (whole cell) for furfural reduction by 4-fold as compared to the control strain, LY180 (pTrc99A) containing empty vector (FIG. 2C). This increase in furfural reduction activity was accompanied by a 50% increase in the minimum inhibitory concentration, from 10 mM furfural to 15 mM furfural (FIG. 2D). Although a smaller increase in activity was observed without inducer, this change was not sufficient to affect the minimum inhibitory concentration.

Combined Effects of fucO Overexpression and Media Supplements.

Figure 3:
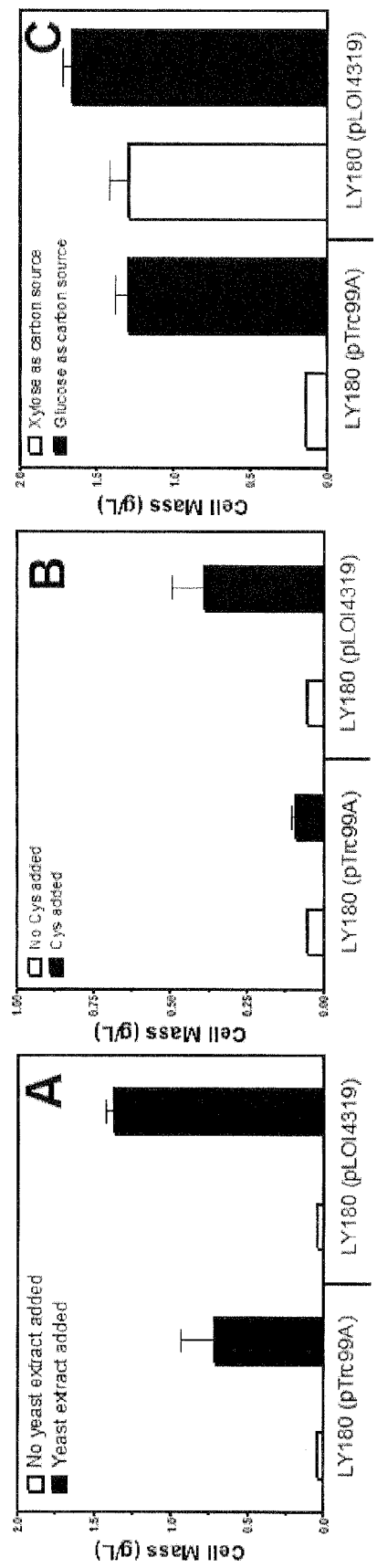
FIGS. 3A-3C. Effects of media supplements and fucO expression on furfural tolerance. Strains LY180(pTrc99A)

Based on the proposed model for furfural inhibition of growth (FIG. 1), overexpression of fucO would be expected to have a combined benefit with other approaches that increase the availability of NADPH. Previous studies (28, 29) have shown that furfural tolerance can be increased by the addition of complex nutrients, cysteine (decreased biosynthetic demand for NADPH), or by the replacement of xylose with glucose (increased NADPH production). LY180 (pTrc99A) and LY180(pLOI4319) were unable to grow in the presence of 15 mM furfural (FIGS. 3A and 3B) without supplements. With supplements, growth was limited and was further increased by the expression of fucO (pLOI4319). With 10 mM furfural, replacement of xylose with glucose substantially restored growth of the control strain LY180 (pTrc99A). Expression of fucO from pLOI4319 provided a small additional benefit with glucose (FIG. 3C).

Expression of fucO Increased Ethanol Production in the Presence of Furfural.

Figure 4:
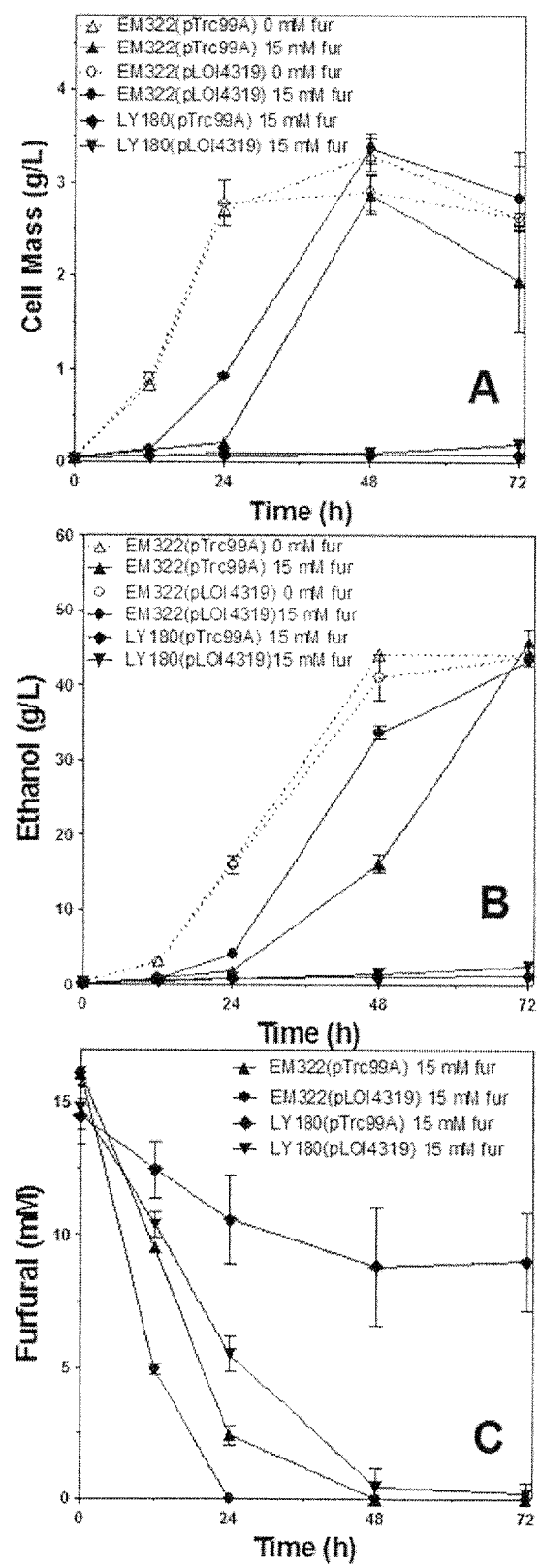
FIGS. 4A-4C. Effect of fucO expression on furfural tolerance during ethanol production from xylose. Batch fermentations were conducted in pH-controlled fermentation vessels in the absence and presence of furfural (15 mM). Expression of fucO from pLOI4319 (0.1 mM IPTG) was compared to vector controls (pTrc99A) using host strains LY180 and EM322. LY180 strains were unable to grow under these conditions but continued to metabolize furfural. Controls were included without furfural (open symbols and dotted lines).

The effect of fucO expression on furfural tolerance was examined during batch fermentations of xylose to ethanol (FIG. 4). Strain LY180(pLOI4319) was unable to grow in the presence of 15 mM furfural, but metabolized furfural at a faster rate than the control containing vector alone. A derivative of LY180 was previously constructed in which yqhD was deleted, denoted strain EM322 (29). After a 24-h lag during which most of the furfural was metabolized, EM322 began to grow and ferment xylose to ethanol. Expression of fucO in EM322(pLOI4319) increased the rate of furfural metabolism, decreased the growth lag, and increased the rate of xylose fermentation to ethanol. Although ethanol production with furfural was improved by expression of fucO, EM322 (pLOI4319) still required longer fermentation times than control strains without furfural. Final ethanol yields (100 g liter$^{-1}$ xylose) for EM322(pLOI4319), and EM322 (pTrc99A) with furfural (15 mM) were similar to those for strains without furfural, approximately 90% of the theoretical maximum. A mutation in yqhD and expression of fucO were both required for the optimal fermentation of broth containing 15 mM furfural.

Expression of fucO Increased Lactate Production in the Presence of Furfural

E. coli strain MM160 is a furfural-resistant derivative of strain LY180. This strain was selected for resistance to hemicellulose hydrolysates of bagasse that contain furfural and other inhibitors (13). Sequencing of a PCR fragment of yqhD from this strain revealed a nonsense mutation (G to A in codon 246, forming a TAG stop codon) that truncates 30% of the YqhD protein. Strain MM160 was re-engineered for D-lactate production and designated strain XW068. This strain was used to examine the effects of fucO expression on lactate production in xylose broth containing furfural. With XW068 (pTrc99A), growth and lactate production from xylose were slowed by the addition of 10 mM furfural (FIGS. 5A, 5B, 5C). Expression of fucO in XW068(pLOI4319) substantially improved both in comparison to the vector control. With 15 mM furfural, only XW068(pLOI4319) was able to grow and ferment xylose (FIGS. 5D, 5E, 5F). Although the control with vector alone continued to metabolize furfural during incubation, minimal growth and lactate production occurred after 120 h. The final yield of D-lactate for XW068 (pLOI4319)

with 15 mM furfural was near that of the control grown without furfural, approximately 85% of the theoretical maximum. Similar beneficial effects of fucO overexpression were also observed with XW059 which was engineered from MM160 for L-lactate production (data not shown). Improved tolerance to the presence of furfural was observed by the overexpression of fucO alone in cells and the cells produced lactate. Introduction of the mutation into yqhD further increased resistance to furfural and also increased production of lactate.

Discussion:

Furfural, the dehydration product of pentose sugars, is an important microbial inhibitor that is formed during dilute acid hydrolysis of hemicelluloses (1, 31). Diverse approaches have been explored for furfural removal such as lime addition (pH 10) (1, 25, 26) and the selection of resistant mutants (1, 21, 29). Developing biocatalysts that are more furfural tolerant would be helpful for the production of renewable products from inedible feedstocks.

Furfuryl alcohol is known to be less toxic than furfural (38, 39). Thus an effective microbial furfural reduction system has the potential to increase furfural resistance. Furfural-resistant strains of *S. cerevisiae* have been isolated (2, 20, 22, 23) and found to exhibit increased expression of aldehyde reductases that may contribute to tolerance. In *E. coli*, many oxidoreductases were also induced by furfural but none originally tested were found to reduce toxicity when overexpressed in the parent strain (28, 29). Two independent, furfural-resistant mutants of *E. coli* were investigated and both were found to have mutations affecting the furfural-inducible yqhD gene encoding a furfural reductase activity. In EMFR9, yqhD expression was silenced by an IS10 insertion into the adjacent regulatory gene (yqhC) (37). In MM160, yqhD was truncated by a nonsense mutation ((13); this study). Deletion of yqhD in the parent strain increased furfural tolerance and overexpression of yqhD in the mutants restored furfural sensitivity (29). A mutation in yqhD alone (EM322) is sufficient to permit growth in xylose broth containing 10 mM furfural (29). The negative effect of YqhD has been attributed to an unusually low Km for NADPH (8 µM), starving essential biosynthetic reactions by depletion of the NADPH pool (FIG. 1).

The discovery of furfural reductase activity in FucO offered an alternative route for furfural reduction to the less toxic alcohol using NADH, an abundant reductant during fermentation. Furfural reduction by this enzyme removed substrate from YqhD and other NADPH-furfural reductases in *E. coli* strains and increased furfural tolerance. Additionally, the combination of fucO expression and silencing of yqhD permitted fermentation in xylose broth containing 15 mM furfural, a concentration similar to that present in hemicellulose hydrolysates of woody biomass (13, 14).

Figure 2:
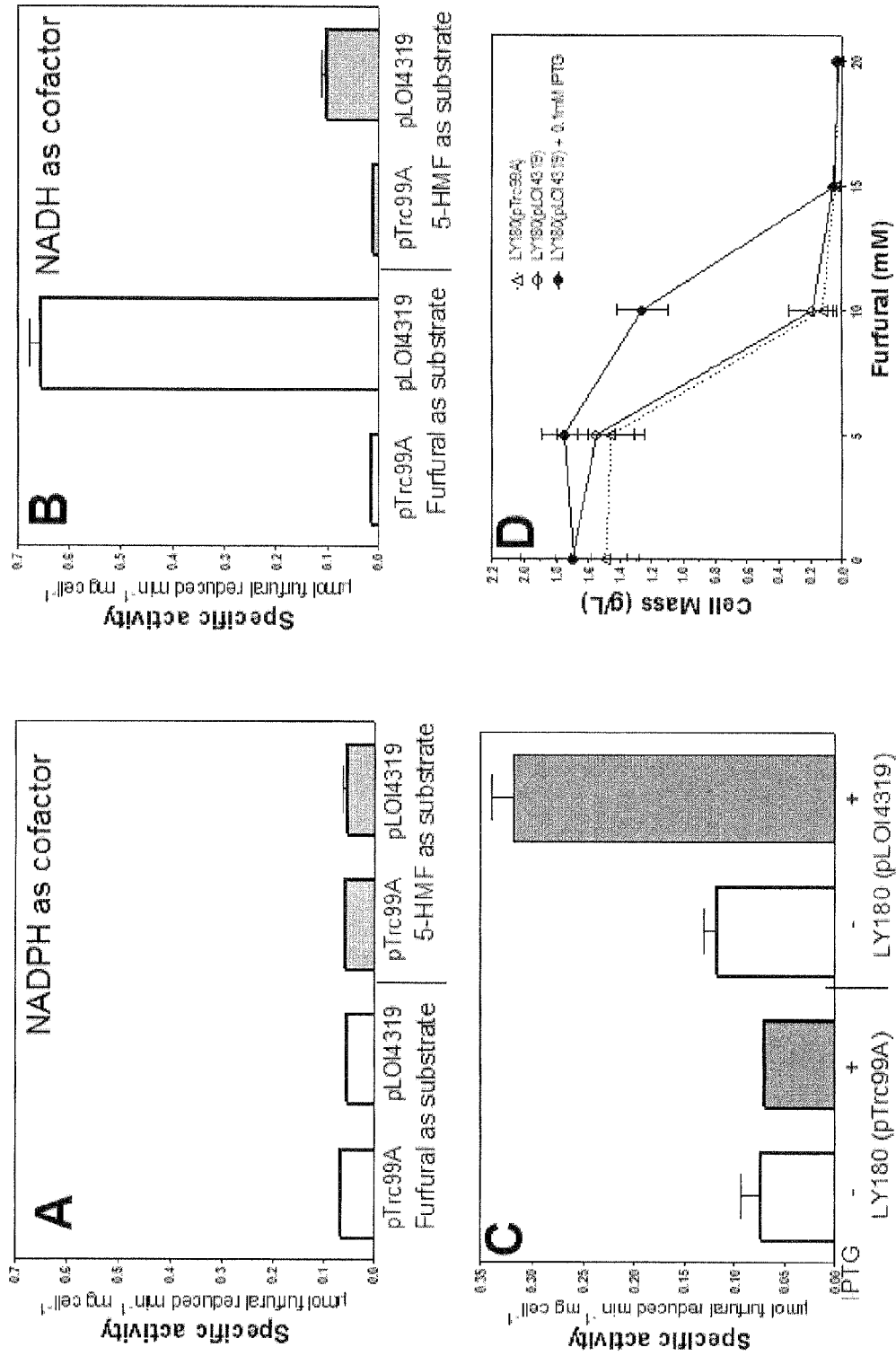
FIGS. 2A-2D. Effect of fucO overexpression in LY180.

FucO belongs to the iron-activated group III dehydrogenase family (33). This enzyme catalyzes the interconversion between L-lactaldehyde and L-1,2-propanediol during the anaerobic dissimilation of fucose (6, 10) and aerobic growth on L-1,2-propanediol (9). FucO has been shown to utilize a broad spectrum of substrates including glycerol, ethylene glycol, L-lactaldehyde, glycoaldehyde, acetaldehyde, glyceraldehyde, propionaldehyde, and methylglyoxal (5, 6, 11) but was not previously known to reduce furans. The sequence of this gene is similar to the iron-containing alcohol dehydrogenase II from *Zymomonas mobilis* and ADH4 from *S. cerevisiae* (11). Although the amino acid identities are quite low, the crystal structure of FucO is very similar to that of YqhD (32, 36), both of which metabolize furfural. FucO and YqhD are each composed of two subunits, with an α/β Rossman nucleotide binding N-terminal domain and an all-α helical C-terminal domain. FucO activity has a $K_m$ value for furfural of 0.4 mM, much lower than that of YqhD (9 mM) (29). The $V_{max}$ of FucO for furfural is only 10% that for L-lactaldehyde (20 µmol min$^{-1}$ mg protein$^{-1}$, 0.035 mM) indicating a strong preference for the native substrate (6). High levels of FucO appear to be needed to increase furfural tolerance in *E. coli*, consistent with the low catalytic rate of furfural reduction. The dehydration product of hexose sugars, 5-HMF, was also metabolized by the FucO enzyme (FIG. 2).

Figure 5:
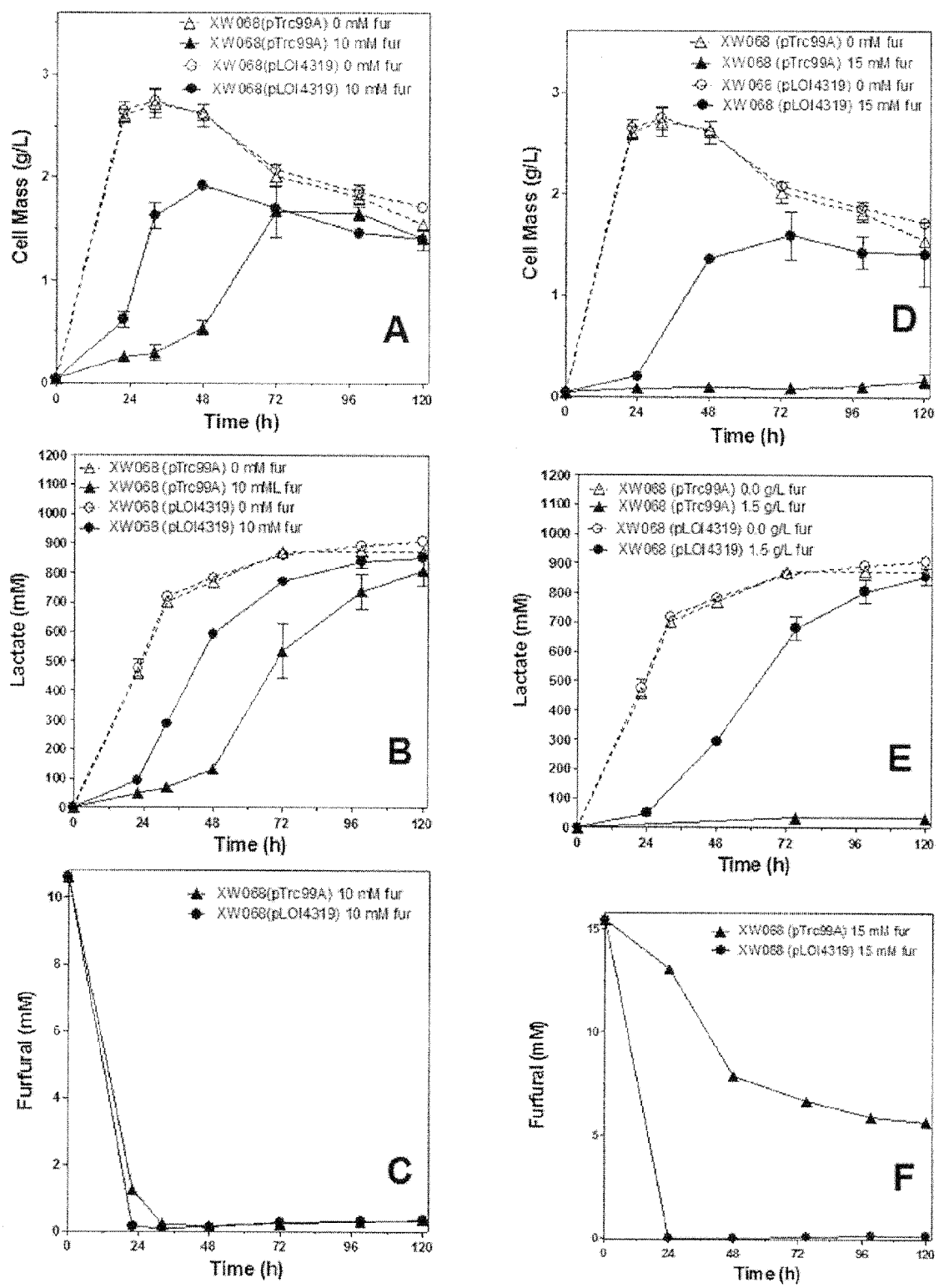
FIGS. 5A-5F. Effect of fucO expression on furfural tolerance during D-lactate production from xylose. Batch fermentations were conducted in pH-controlled fermentation vessels in the absence and presence of furfural. Expression of fucO from pLOI4319 (0.1 mM IPTG) was compared to vector controls (pTrc99A) using XW068 as the host. Controls were included without furfural (open symbols and dotted lines).

Overexpression of an NADH-dependent furfural reductase provides a detoxification strategy that may be generally useful for other enteric microbial catalysts (FIG. 1). NADPH-dependent reductases are widely used for detoxification processes and appear best suited for aerobic growth where NADPH is more abundant. NADPH-dependent activities could be replaced with NADH-dependent activities in biocatalysts designed for anaerobic fermentation products. Our studies have demonstrated the utility of this approach both for ethanol production and lactate production using engineered strains of *E. coli* (FIGS. 4 and 5). When combined with other approaches that increase the availability of NADPH, overexpression of fucO can provide a further benefit for furfural tolerance. An analogous strategy that minimizes the depletion of NADPH pools during detoxification process may be generally useful for other toxic agents in lignocellulosic sugar streams and with other organisms.

Example 2

Alteration of FucO Activity for the Production of Succinate

In this example, succinate-producing biocatalysts that can ferment xylose effectively and have increased resistance to furfural, a toxic compound present in xylose-rich hemicellulose hydrolysates (dilute acid hydrolysis, 160-190 C) were constructed. Strain KJ122 is an excellent biocatalysts designed to ferment glucose to succinate (17, 40, 42). In this study, we adapted strains that grow well on xylose. This strain has been further engineered for furfural tolerance by deleting or silencing the yqhD gene encoding a NADPH-dependent furfural reductase, an activity that depletes the NADPH pool needed for biosynthesis and growth. In addition, we demonstrate a second gene fucO that alone or in combination with the yqhD deletion provide increased tolerance to furfural.

The fucO gene normally functions in fucose degradation. We have discovered that the FucO enzyme can use furfural and 5-hydroxymethylfurfural as a substrate. Both are reduced to their respective alcohols using NADH as the reductant. NADH is an abundant cofactor during fermentative growth.

Materials and Methods

Strains, Plasmids Media and Growth Conditions

Strains, plasmids and primers used in this example are listed in Table 2. Cultures were grown aerobically in Luria broth containing 2% (w/v) glucose or 5% (w/v) arabinose during strain constructions. Ampicillin (50 mg liter$^{-1}$), kanamycin (50 mg liter$^{-1}$), or chloramphenicol (40 mg liter$^{-1}$) were added as appropriate. KJ122 was previously engineered for efficient succinate production from glucose (17, 43). After approximately 50 generations (approximately 10 sequential transfers) in AM1 100 g liter$^{-1}$ xylose media, this strain fermented xylose to succinate. A clone was isolated at the end of this adaptation and designated strain XW055. Strain XW055 ferments xylose to succinate as efficiently as KJ122 ferments glucose to succinate.

Two Genes

The yqhD ORF in XW055 was deleted to generate strain XW056. The *E. coli* fucO ORFs were integrated under adhE promoters and ribosomal binding sites into the chromosomes of XW055 and XW056 to construct strains XW057 and XW081. Red recombinase technology (Gene Bridges GmbH, Dresden, Germany) was used to facilitate chromosomal integration as previously described (17, 19, 40, 41). The plasmids used in strain construction were generated as previously described (17, 19, 40, 41). CloneEZ® PCR Cloning Kit (GenScript, Piscataway, N.J., USA) was used to construct the plasmid pLOI5209 containing fucO ORF exactly replacing adhE ORF.

Furfural Toxicity Measurement

Furfural toxicity was measured using tube cultures (13 by 100 mm) containing 4 ml of AM1 media with 50 g liter$^{-1}$ (w/v) xylose, 50 mM KHCO$_3$, 100 mM MOPS pH 7, and 10 mM furfural. Cultures were inoculated to an initial density of 44 mg dew liter$^{-1}$. Cell mass was measured at 550 nm after incubation for 48 h at 37° C.

Results and Discussion

Figure 6:
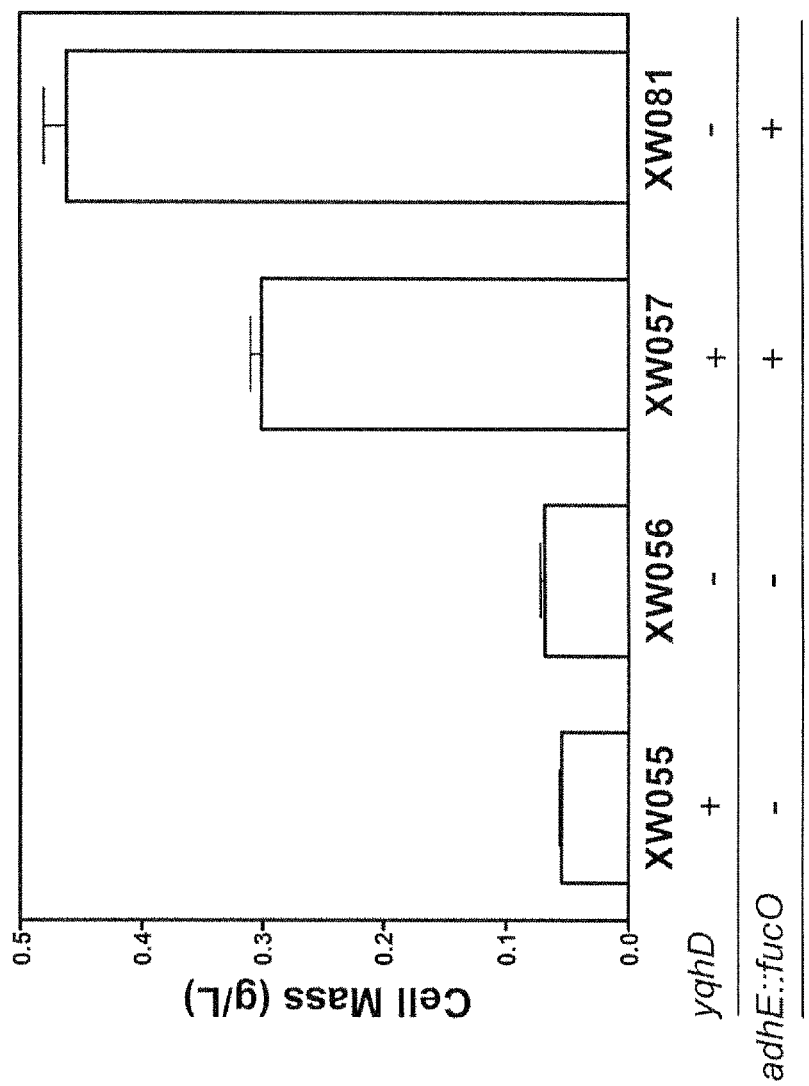
FIG. 6. Chromosomal integration adhE:: fucO increased furfural resistance for succinate producing *E. coli* strains. The strains XW055, XW056, XW057 and XW081 were grown in AM1 medium, 50 g xylose, 100 mM MOPS (pH 7.0), 50 mM KHCO$_3$ in the presence of 10 mM furfural for 48 h at 37° C. The genetic features about yqhD and fucO integration are indicated below the graphs.

With fucO integrated under adhE promoter, the modified strain XW057 showed more furfural resistance than its parent strain XW055 (FIG. 6). The deletion of yqhD alone only showed very limited benefit in furfural resistance (FIG. 6). Interestingly, the two genetic modifications together, deletion of yqhD and fucO integration, showed the greatest resistance to furfural and there was an approximately 10-fold increase in cell mass compared to the parent strain XW055 in the presence of 10 mM furfural (FIG. 6).

This result is consistence with the discoveries obtained in *E. coli* strains engineered for ethanol production (EM322) and lactate production (XW0059 and XW068). XW055 is derived from *E. coli* C (ATCC8739) and EM322, XW059 and XW068 are derived from *E. coli* W (ATCC9637). This suggests fucO expression together with yqhD deletion as a general furfural detoxification approach that can be applied in different *E. coli* strains producing different products.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

TABLE 1

Bacterial strains, plasmids, and primers

| Strains, plasmids, or primers | Relevant characteristics | Reference of source |
|---|---|---|
| Strains | | |
| LY180 | ΔfrdBC::(Zm frg celY$_{Ec}$), ΔldhA::(Zm frg casB$_{Ko}$), adhE::(Zm frg estZ$_{Pp}$ FRT), ΔackA::FRT, rrlE::(pdc adhA adhB FRT), ΔmgsA::FRT | (29) |
| EM322 | LY180 ΔyqhD::FRT | (29) |
| BL21 (λDE3) | F$^-$ ompT gal dcm lon hsdS$_B$(r$_B^-$ m$_B^-$) λ(DE3 [lacI lacUV5-T7 gene 1 ind1 sam7 nin5]) | Promega, Madison, WI |
| MM160 | Hydrolysate resistant derivative of LY180, yqhD frame shift | (13) |
| XW042 | MM160 ldhA::ldhL, Δ(rrlE::[pdc adhA adhB FRT], Δ(Zm frg estZ$_{Pp}$ FRT) L-lactate production | This study |
| XW043 | MM160 ldhA restored, Δ(rrlE::[pdc adhA adhB FRT]), Δ(Zm frg estZPp FRT) D-lactate production | This study |
| XW059 | XW042 after serial transfer with xylose L-lactate production | This study |
| XW068 | XW043 after serial transfer with xylose D-lactate production | This study |
| Plasmids | | |
| pTrc99A | pTrc bla oriR rrnB lacI$^q$ | (4) |
| pCR2.1 | TOPO cloning vector | Invitrogen |
| pLOI4162 | PacI flanked cat-sacB cassette | (17) |
| pET15b | T7 expression vector | Novagen |
| fucO cloning and expression | | |
| pLOI4319 | fucO in pTrc99A | This study |
| pLOI4322 | fucO in pET15b | This study |

TABLE 1-continued

Bacterial strains, plasmids, and primers

| Strains, plasmids, or primers | Relevant characteristics | Reference of source |
|---|---|---|
| Deletion of (rrlE::[pdc adhA adhB FRT]) | | |
| pLOI4780 | pdc-adhA-adhB from LY180 cloned into pCR2.1-TOPO vector | This study |
| pLOI4781 | cat-sacB cassette cloned into pdc-adhA-adhB in pLOI4780 | This study |
| pLOI4782 | PacI digestion of pLOI4781; self-ligated to delete pdc-adhA-adhB | This study |
| Deletion of (adhE::[Zm frg estZ$_{Pp}$ FRT]) | | |
| pLOI4811 | (adhE::[Zm frg est ZPp FRT) region cloned into pCR2.1-TOPO vector | This study |
| pLOI4824 | cat-sacB cassette cloned into the adhE::(Zm frg estZPp FRT) region of pLOI4811 | This study |
| pLOI5167 | E. coli adhE ORF and its adjacent regions cloned into pCR2.1 TOPO vector | This study |
| pLOI5168 | cat-sacB cassette cloned into adhE in pLOI5167 | This study |
| pLOI5169 | PacI digested of pLOI5168; self-ligated to delete adhE | This study |
| ldhA restoring | | |
| pLOI4652 | ldhA (PCR) from E. coli cloned into the pCR2.1-TOPO vector | (40) |
| pLOI4653 | cat-sacB cassette cloned into ldhA of pLOI4652 | (40) |
| lhdL integration | | |
| pLOI5161 | ldhA ORF and its adjacent regions cloned into pCR2.1 TOPO vector | This study |
| pLOI5174 | ldhL ORF from TG108 was cloned and used to replace the ldhA ORF in pLOI5161 | This study |
| Primers fucO cloning | | |
| fucO for EcoRI | CGCGCGGAATTCGATTGCCGTAGTGCTGGAGA (SEQ ID NO: 3) | This study |
| fucO rev BamHI | CGCGCGGGATCCTGCGGTTGGTACGGTAACGG (SEQ ID NO: 4) | This study |
| ldaA and ldhL integration | | |
| ldhA for | GATAACGGAGATCGGGAATG (SEQ ID NO: 5) (for construction of pLOI4652) | (40) |
| ldhA rev | CTTTGGCTGTCAGTTCACCA (SEQ ID NO: 6) (for construction of pLOI4652) | (40) |
| ldhA-1 | TCTGGAAAAAGGCGAAACCT (SEQ ID NO: 7) (for construction of pLOI4653) | (40) |
| ldhA-2 | TTTGTGCTATAAACGGCGAGT (SEQ ID NO: 8) (for construction of pLOI4653) | (40) |
| ldhL ORF up | ATGTCTAATATTCAAAATCATCAAAAAGTTGTCCTCGTCG (SEQ ID NO: 9) (for construction of pLOI5174) | This study |

TABLE 1-continued

Bacterial strains, plasmids, and primers

| Strains, plasmids, or primers | Relevant characteristics | Reference of source |
|---|---|---|
| ldhL ORF down | TTATTTGTCTTGTTTTTCAGCAAGAGCGTTTAGAC (SEQ ID NO: 10) (for construction of pLOI5174) | This study |
| ldhA rev1 | AAGACTTTCTCCAGTGATGTTGAATCAC (SEQ ID NO: 11) (for construction of pLOI5174) | This study |
| ldhA for1 | TCTTGCCGCTCCCCT (SEQ ID NO: 12) (for construction of pLOI5174) | This study |
| Deletion of (rrlE:: [pdc adhA adhB FRT]) | | |
| pdc for | TGGTCTCAAGCATCACTTCG (SEQ ID NO: 13) | This study |
| adhB rev | TTGGTCAGAGCACAAGCATC (SEQ ID NO: 14) | This study |
| adhB-1 | CCCACGCATTTGAAGCTTAT (SEQ ID NO: 15) | This study |
| pdc-2 | ATCGATTTTAGCCGGAGCTT (SEQ ID NO: 16) | This study |
| Deletion of (Zm frg estZ$_{Pp}$ FRT) | | |
| estZ for | ACTGGCATCTGAGTTCTCTG (SEQ ID NO: 17) | This study |
| estZ rev | TTCCATGGCGTGAGTTACTG (SEQ ID NO: 18) | This study |
| estZ-1 | CAGACCGTGCGGAATATGGA (SEQ ID NO: 19) | This study |
| estZ-2 | CAGCCTCGATTCGCATGACA (SEQ ID NO: 20) | This study |
| adhE for | CAATACGCCTTTTGACAGCA (SEQ ID NO: 21) | This study |
| adhE rev | GCCATCAATGGCAAAAAGTT (SEQ ID NO: 22) | This study |
| adhE-1 | TCAGTAGCGCTGTCTGGCA (SEQ ID NO: 23) | This study |
| adhE-2 | AATGCTCTCCTGATAATGTTAAACTTTTTAGTA (SEQ ID NO: 24) | This study |
| Amplification and sequencing of yqhD region | | |
| yqhD for | TATGATGCCAGGCTCGTACA (SEQ ID NO: 25) | This study |
| yqhD rev | GATCATGCCTTTCCATGCTT (SEQ ID NO: 26) | This study |

TABLE 2

Bacterial strains, plasmids, and primers

| Strains, plasmids, or primers | Relevant characteristics | Reference of source |
|---|---|---|
| Stains | | |
| LY180 | ΔfrdBC::(Zm frg celY$_{Ec}$), ΔldhA::(Zm frg casB$_{Ko}$), adhE::(Zm frg estZ$_{Pp}$ FRT), ΔackA::FRT, rrlE::(pdc adhA adhB FRT), ΔmgsA::FRT | (29) |
| EM322 | LY180 ΔyqhD::FRT | (29) |
| MM160 | Hydrolysate resistant derivative of LY180, yqhD (TGG [Trp246] to TAG [Stop]) | (13), this study |
| KJ122$^a$ | ΔldhA, ΔadhE, Δ(focA-pflB), ΔackA, ΔmgsA, ΔpoxB, ΔsfcA, ΔaspC, ΔcitF, ΔtdcDE | (17, 40, 42) |
| XW055 | KJ122 after serial transfer with xylose for succinate production | This study |
| XW056 | XW055 ΔyqhD | This study |
| XW057 | XW055 adhE::fucO | This study |
| XW081 | XW057 ΔyqhD | This study |
| Plasmids | | |
| pCR2.1 | TOPO cloning vector | Invitrogen |
| pLOI4162 | PacI flanked cat-sacB cassette | (17) |
| Deletion of yqhD | | |
| pLOI5203 | yqhD ORF and its adjacent regions cloned into pCR2.1 TOPO vector | This study |
| pLOI5204 | cat-sacB cassette cloned into yqhD in pLOI5203 | This study |
| pLOI5205 | PacI digestion of pLOI5204; self-ligated to delete yqhD | This study |
| adhE::fucO integration | | |
| pLOI5167 | *E. coli* adhE ORF and its adjacent regions cloned into pCR2.1 TOPO vector | This study |
| pLOI5168 | cat-sacB cassette cloned into adhE in pLOI5167 | This study |
| pLOI5209 | adhE ORF was exactly replaced by fucO ORF in pLOI5167 | This study |
| Primers Deletion of yqhD | | |
| yqhD for | TATGATGCCAGGCTCGTACA (SEQ ID NO: 25) | This study |
| yqhD rev | GATCATGCCTTTCCATGCTT (SEQ ID NO: 26) | This study |
| yqhD-1 | GCTTTTTACGCCTCAAACTTTCGT (SEQ ID NO: 27) | This study |
| yqhD-2 | TACTTGCTCCCTTTGCTGG (SEQ ID NO: 28) | This study |
| adhE::fucO integration | | |
| adhE for | CAATACGCCTTTTGACAGCA (SEQ ID NO: 21) | This study |
| adhE rev | GCCATCAATGGCAAAAGTT (SEQ ID NO: 22) | This study |
| adhE-1 | TCAGTAGCGCTGTCTGGCA (SEQ ID NO: 23) | This study |

TABLE 2-continued

Bacterial strains, plasmids, and primers

| Strains, plasmids, or primers | Relevant characteristics | Reference of source |
|---|---|---|
| adhE-2 | AATGCTCTCCTGATAATGTTAAACTTTTTTAGTA (SEQ ID NO: 24) | This study |
| adhE-fucO ORF for | AATGCTCTCCTGATAATGTTAAACTTTTTTAGTAATGATGGCTAACAGAATGATTCTGAAC (SEQ ID NO: 29) | This study |
| adhE-fucO ORF rev | TGCCAGACAGCGCTACTGATTACCAGGCGGTATGGTAAAG (SEQ ID NO: 30) | This study |
| adhE-fucO-1 | CTTTACCATACCGCCTGGTAATCAGTAGCGCTGTCTGGCA (SEQ ID NO: 31) | This study |
| adhE-fucO-2 | GTTCAGAATCATTCTGTTAGCCATCATTACTAAAAAAGTTTAACATTATCAGGAGAGCATT (SEQ ID NO: 32) | This study |

$^a$The precursor of strain KJ122 also contains spontaneous mutations in pck, ptsI, and affecting galP that were acquired during selection for improvements in growth (17, 40, 42).

REFERENCES

1. Almeida, J. R., M. Bertilsson, M. F. Gorwa-Grauslund, S. Gorsich, and G. Liden. 2009. Metabolic effects of furaldehydes and impacts on biotechnological processes. Appl. Microbiol. Biotechnol. 82:625-638.
2. Almeida, J. R., A. Roder, T. Modig, B. Laadan, G. Liden, and M. F. Gorwa-Grauslund. 2008. NADH- vs NADPH-coupled reduction of 5-hydroxymethyl furfural (HMF) and its implications on product distribution in Saccharomyces cerevisiae. Appl. Microbiol. Biotechnol. 78:939-945.
3. Alvira, P., E. Tomas-Pejo, M. Ballesteros, and M. J. Negro. 2010. Pretreatment technologies for an efficient bioethanol production process based on enzymatic hydrolysis: A review. Bioresour. Technol. 101:4851-4861.
4. Amann, E., B. Ochs, and K. J. Abel. 1988. Tightly regulated tac promoter vectors useful for the expression of unfused and fused proteins in Escherichia coli. Gene 69:301-315.
5. Blikstad, C., and M. Widersten. 2010. Functional characterization of a stereospecific diol dehydrogenase, FucO, from Escherichia coli: Substrate specificity, pH dependence, kinetic isotope effects and influence of solvent viscosity. Journal of Molecular Catalysis B-Enzymatic 66:148-155.
6. Boronat, A., and J. Aguilar. 1979. Rhamnose-induced propanediol oxidoreductase in Escherichia coli: purification, properties, and comparison with the fucose-induced enzyme. J. Bacteriol. 140:320-326.
7. Carole, T. M., J. Pellegrino, and M. D. Paster. 2004. Opportunities in the industrial biobased products industry. Appl. Biochem. Biotechnol. 113-116:871-885.
8. Chen, Y. M., and E. C. C. Lin. 1984. Dual control of a common L-1,2-propanediol oxidoreductase by L-fucose and L-rhamnose in Escherichia coli. J. Bacteriol. 157:828-832.
9. Chen, Y. M., Z. Lu, and E. C. Lin. 1989. Constitutive activation of the fucAO operon and silencing of the divergently transcribed fucPIK operon by an IS5 element in Escherichia coli mutants selected for growth on L-1,2-propanediol. J. Bacteriol. 171:6097-6105.
10. Cocks, G. T., J. Aguilar, and E. C. C. Lin. 1974. Evolution of L-1,2-propanediol catabolism in Escherichia coli by recruitment of enzymes for L-fucose and L-lactate metabolism. J. Bacteriol. 118:83-88.
11. Conway, T., and L. O. Ingram. 1989. Similarity of Escherichia coli propanediol oxidoreductase (fucO product) and an unusual alcohol dehydrogenase from Zymomonas mobilis and Saccharomyces cerevisiae. J. Bacteriol. 171:3754-3759.
12. Frick, O., and C. Wittmann. 2005. Characterization of the metabolic shift between oxidative and fermentative growth in Saccharomyces cerevisiae by comparative 13 C flux analysis. Microb. Cell. Fact. 4:30.
13. Geddes, C. C., M. T. Mullinnix, I. U. Nieves, J. J. Peterson, R. W. Hoffman, S. W. York, L. P. Yomano, E. N. Miller, K. T. Shanmugam, and L. O. Ingram. 2010. Simplified process for ethanol production from sugarcane bagasse using hydrolysate-resistant Escherichia coli strain MM160. Bioresour. Technol. 102:2702-2711,
14. Geddes, C. C., J. J. Peterson, C. Roslander, G. Zacchi, M. T. Mullinnix, K. T. Shanmugam, and L. O. Ingram. 2010. Optimizing the saccharification of sugar cane bagasse using dilute phosphoric acid followed by fungal cellulases. Bioresour. Technol. 101:1851-1857.
15. Grabar, T. B., S. Zhou, K. T. Shanmugam, L. P. Yomano, and L. O. Ingram. 2006. Methylglyoxal bypass identified as source of chiral contamination in L(+) and D(−)-lactate fermentations by recombinant Escherichia coli. Biotechnol. Lett. 28:1527-1535.
16. Crabowska, D., and A. Chelstowska. 2003. The ALD6 gene product is indispensable for providing NADPH in yeast cells lacking glucose-6-phosphate dehydrogenase activity. J. Biol. Chem. 278:13984-13988.
17. Jantama, K., X. Zhang, J. C. Moore, K. T. Shanmugam, S. A. Svoronos, and L. O. Ingram. 2008. Eliminating side products and increasing succinate yields in engineered strains of Escherichia coli C. Biotechnol. Bioeng. 101:881-893.
18. Jarboe, L. R., T. B. Grabar, L. P. Yomano, K. T. Shanmugam, and L. O. Ingram. 2007. Development of ethanologenic bacteria. Adv. Biochem. Eng Biotechnol. 108:237-261.
19. Jarboe, L. R., X. Zhang, X. Wang, J. C. Moore, K. T. Shanmugam, and L. O. Ingram. 2010. Metabolic engineering for production of biorenewable fuels and chemicals: contributions of synthetic biology. J. Biomed. Biotechnol. 2010:761042.

20. Laadan, B., J. R. Almeida, P. Radstrom, B. Hahn-Hagerdal, and M. Gorwa-Grauslund. 2008. Identification of an NADH-dependent 5-hydroxymethylfurfural-reducing alcohol dehydrogenase in *Saccharomyces cerevisiae*. Yeast 25:191-198.
21. Liu, Z. L. 2006. Genomic adaptation of ethanologenic yeast to biomass conversion inhibitors. Appl. Microbiol. Biotechnol. 73:27-36.
22. Liu, Z. L., and J. Moon. 2009. A novel NADPH-dependent aldehyde reductase gene From *Saccharomyces cerevisiae* NRRL Y-12632 involved in the detoxification of aldehyde inhibitors derived from lignocellulosic biomass conversion. Gene 446:1-10.
23. Liu, Z. L., J. Moon, B. J. Andersh, P. J. Slininger, and S. Weber. 2008. Multiple gene-mediated NAD(P)H-dependent aldehyde reduction is a mechanism of in situ detoxification of furfural and 5-hydroxymethylfurfural by *Saccharomyces cerevisiae*. Appl. Microbiol. Biotechnol. 81:743-753.
24. Martinez, A., T. B. Grabar, K. T. Shanmugam, L. P. Yomano, S. W. York, and L. O. Ingram. 2007. Low salt medium for lactate and ethanol production by recombinant *Escherichia coli* B. Biotechnol. Lett. 29:397-404.
25. Martinez, A., M. E. Rodriguez, M. L. Wells, S. W. York, J. F. Preston, and L. O. Ingram. 2001. Detoxification of dilute acid hydrolysates of lignocellulose with lime. Biotechnol. Prog. 17:287-293.
26. Martinez, A., M. E. Rodriguez, S. W. York, J. F. Preston, and L. O. Ingram. 2000. Effects of Ca(OH)(2) treatments ("overliming") on the composition and toxicity of bagasse hemicellulose hydrolysates. Biotechnol. Bioeng. 69:526-536.
27. Martinez, A., M. E. Rodriguez, S. W. York, J. F. Preston, and L. O. Ingram. 2000. Use of UV absorbance to monitor furans in dilute acid hydrolysates of biomass. Biotechnol. Prog. 16:637-641.
28. Miller, E. N., L. R. Jarboe, P. C. Turner, P. Pharkya, L. P. Yomano, S. W. York, D. Nunn, K. T. Shanmugam, and L. O. Ingram. 2009. Furfural inhibits growth by limiting sulfur assimilation in ethanologenic *Escherichia coli* strain LY180. Appl. Environ. Microbiol. 75:6132-6141.
29. Miller, E. N., L. R. Jarboe, L. P. Yomano, S. W. York, K. T. Shanmugam, and L. O. Ingram. 2009. Silencing of NADPH-dependent oxidoreductase genes (yqhD and dkgA) in furfural-resistant ethanologenic *Escherichia coli*. Appl. Environ. Microbiol. 75:4315-4323.
30. Miller, E. N., P. C. Turner, L. R. Jarboe, and L. O. Ingram. 2010. Genetic changes that increase 5-hydroxymethyl furfural resistance in ethanol-producing *Escherichia coli* LY180. Biotechnol. Lett. 32:661-667.
31. Mills, T. Y., N. R. Sandoval, and R. T. Gill. 2009. Cellulosic hydrolysate toxicity and tolerance mechanisms in *Escherichia coli*. Biotechnol. Biofuels. 2:26.
32. Montella, C., L. Bellsolell, R. Perez-Luque, J. Badia, L. Baldoma, M. Coll, and J. Aguilar. 2005. Crystal structure of an iron-dependent group III dehydrogenase that interconverts L-lactaldehyde and L-1,2-propanediol in *Escherichia coli*. J. Bacteriol. 187:4957-4966,
33. Reid, M. F., and C. A. Fewson. 1994. Molecular characterization of microbial alcohol dehydrogenases. Crit. Rev. Microbiol. 20:13-56.
34. Runquist, D., B. Hahn-Hagerdal, and M. Bettiga. 2009. Increased expression of the oxidative pentose phosphate pathway and gluconeogenesis in anaerobically growing xylose-utilizing *Saccharomyces cerevisiae*. Microb. Cell. Fact. 8:49.
35. Saha, B. C. 2003. Hemicellulose bioconversion. J. Ind. Microbiol. Biotechnol. 30:279-291.
36. Sulzenbacher, G., K. Alvarez, R. H. H. van den Heuvel, C. Versluis, M. Spinelli, V. Campanacci, C. Valencia, C. Cambillau, H. Eklund, and M. Tegoni. 2004. Crystal structure of *E. coli* alcohol dehydrogenase YqhD: evidence of a covalently modified NADP coenzyme. J. Mol. Biol. 342:489-502.
37. Turner, P. C., E. N. Miller, L. R. Jarboe, C. L. Baggett, K. T. Shanmugam, and L. O. Ingram. 2010. YqhC regulates transcription of the adjacent *Escherichia coli* genes yqhD and dkgA that are involved in furfural tolerance. J. Ind. Microbiol. Biotechnol. doi:10.1007/s10295-010-0787-5.
38. Zaldivar, J., A. Martinez, and L. O. Ingram. 2000. Effect of alcohol compounds found in hemicellulose hydrolysate on the growth and fermentation of ethanologenic *Escherichia coli*. Biotechnol. Bioeng. 68:524-530.
39. Zaldivar, J., A. Martinez, and L. O. Ingram. 1999. Effect of selected aldehydes on the growth and fermentation of ethanologenic *Escherichia coli*. Biotechnol. Bioeng. 65:24-33.
40. Zhang, X., K. Jantama, K. T. Shanmugam, and L. O. Ingram. 2009. Reengineering *Escherichia coli* for succinate production in mineral salts medium. Appl. Environ. Microbiol. 75:7807-7813.
41. Zhang, X., K. T. Shanmugam, and L. O. Ingram. 2010. Fermentation of glycerol to succinate by metabolically engineered strains of *Escherichia coli*. Appl. Environ. Microbiol. 76:2397-2401.
42. Zhang, X., K. Jantama, J. C. Moore, L. R. Jarboe, K. T. Shanmugam, and L. O. Ingram. 2009. Metabolic evolution of energy-conserving pathways for succinate production in *Escherichia coli*. Proc. Natl. Acad. Sci. U.S.A. 106:20180-20185.
43. Jantama, K., M. J. Haupt, S. A. Svoronos, X. Zhang, J. C. Moore, K. T. Shanmugam, and L. O. Ingram. 2008. Combining metabolic engineering and metabolic evolution to develop nonrecombinant strains of *Escherichia coli* C that produce succinate and malate. Biotechnol. Bioeng. 99:1140-1153.

We claim:

1. An isolated bacterial, fungal or yeast cell having increased NADH-dependent propanediol oxidoreductase (FucO) activity as compared to a reference bacterial, fungal or yeast cell, wherein said bacterial, fungal or yeast cell having increased FucO activity reduces furfural and/or 5-hydroxymethylfurfural (5-HMF) to their respective alcohols and wherein the isolated bacterial, fungal or yeast cell also comprises modification to a yqhD gene, a yqhC gene and/or a dkgA gene which causes decreased activity of a YqhD protein, decreased activity of a YqhC protein and/or decreased activity of a DkgA protein in the cell compared to the reference bacterial, fungal or yeast cell.

2. The isolated bacterial, fungal or yeast cell of claim 1, wherein said bacterial, fungal or yeast cell produces a desired product, or is genetically engineered to produce a desired product, selected from the group consisting of ethanol, lactic acid, succinic acid, malic acid, acetic acid, 1,3-propanediol, 2,3-propanediol, 1,4-butanediol, 2,3-butanediol, butanol, pyruvate, dicarboxylic acids, adipic acid and amino acids.

3. The isolated bacterial, fungal or yeast cell of claim 1, wherein said bacterial, fungal or yeast cell exhibits increased production of said desired product as compared to a reference bacterial, fungal or yeast cell in the presence of furfural and/or 5-hydroxymethylfurfural (5-HMF).

4. The isolated bacterial cell of claim 1, wherein:
 a) expression of the yqhD gene is reduced in said bacterial cell as compared to a reference bacterial cell;
 b) expression of the dkgA gene is reduced in said bacterial cell as compared to a reference bacterial cell;
 c) expression of the yqhD gene, yqhC gene and/or the dkgA gene are reduced in said bacterial cell as compared to expression in a reference bacterial cell;
 d) expression of the yqhC gene is reduced in said bacterial cell as compared to expression in a reference bacterial cell;
 e) expression of the yqhD gene, the yqhC gene and the dkgA gene is reduced in said bacterial cell as compared to expression in a reference bacterial cell;
 f) the yqhD gene is not expressed or is deleted in said bacterial cell;
 g) the yqhD gene and the dkgA gene are not expressed or are deleted in said bacterial cell;
 h) the yqhC gene or yqhD gene or the yqhC gene and the dkgA gene are not expressed or are deleted in said bacterial cell;
 i) the yqhC gene is not expressed or is deleted in said bacterial cell;
 j) expression of the dkgA gene is reduced in said bacterial cell as compared to a reference bacterial cell;
 k) the dkgA gene is not expressed in said bacterial cell;
 l) the activity of the yqhD gene, yqhC gene and/or the dkgA gene product(s) are reduced in said bacterial cell as compared to expression in a reference bacterial cell; or
 m) the activity of the yqhC gene product is reduced in said bacterial cell as compared to expression in a reference bacterial cell.

5. The isolated bacterial, fungal or yeast cell of claim 1, wherein FucO activity is increased by:
 a) expressing the FucO gene in a plasmid or a multicopy plasmid with a native promoter or a promoter sequence;
 b) transposon integration of additional copies of the FucO gene within the chromosome of a bacterial, fungal or yeast cell;
 c) replacement of the FucO gene native promoter with a promoter that increases the level of gene expression in a bacterial cell; or
 d) the FucO enzyme is mutated to increase catalytic efficiency or reduce its Km.

6. The isolated bacterial cell of claim 1, wherein said bacterial cell is a Gram-negative or a Gram-positive bacterial cell.

7. The isolated bacterial cell according to claim 6, wherein the Gram-negative bacterial cell is a bacterial cell selected from the genera of *Escherichia, Zymomonas, Acinetobacter, Gluconobacter, Geobacter, Shewanella, Salmonella, Enterobacter* or *Klebsiella* and the Gram-positive bacterial cell is selected from the genera of *Bacillus, Clostridium,* Corynebacterial cell, *Lactobacillus, Lactococcus, Oenococcus, Streptococcus* and Eubacterial.

8. The isolated bacterial cell of claim 7, wherein the bacterial cell is *Escherichia coli* or *Klebsiella oxytoca*.

9. The isolated bacterial cell of claim 8, wherein said bacterial cell is selected from *Thermoanaerobes, Bacillus* spp., *Paenibacillus* spp. or *Geobacillus* spp.

10. The isolated yeast cell of claim 1, wherein said yeast cell is a *Candida, Hansenula, Kluyveromyces, Pichia, Saccharomyces, Schizosaccharomyces,* or *Yarrowia* cell.

11. The isolated yeast cell of claim 10, wherein said yeast cell is *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica*.

12. The isolated fungal cell of claim 1, wherein said fungal cell is a *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

13. The isolated fungal cell of claim 12, wherein said fungal cell is an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis sub-*

*vermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes Trametes versicolor, Trichoderma harzianum, Trichoderma koningii, Trichoderma longibrachiatum, Trichoderma reesei,* or *Trichoderma viride* cell.

14. An isolated bacterial, fungal or yeast cell having increased FucO activity wherein said bacterial, fungal or yeast cell is capable of producing a desired product, or has been genetically engineered to produce a desired product, wherein the isolated bacterial, fungal or yeast cell further comprises modification to NADPH-dependent aldehyde reductase (yqhD) gene which causes decreased activity of YqhD protein in the bacterial, fungal or yeast cell compared to the reference bacterial, fungal or yeast cell, and wherein said bacterial, fungal or yeast cell is prepared by a process comprising: a) growing a candidate mutant strain of the bacterial, fungal or yeast cell capable of producing a desired product, or which has been genetically engineered to produce a desired product, in the presence of furfural or 5-hydroxymethylfurfural (5-HMF); and b) selecting mutants that produce a desired product in the presence of about 5 mM to about 40 mM, about 5 mM to about 20 mM, about 15 to about 30 mM, furfural and/or 5-hydroxymethylfurfural (5-HMF).

15. The isolated bacterial cell of claim 4, wherein expression of the yqhD gene is reduced in said bacterial cell as compared to a reference bacterial cell.

16. The isolated bacterial cell of claim 4, wherein the yqhD gene has been deleted from the genome of said bacterial cell.

17. The isolated bacterial strain of claim 1, wherein the activity of the YqhD protein is reduced by at least 95% as compared to a reference bacterial strain.

18. The isolated bacterial strain of claim 17, wherein the activity of the YqhD protein is reduced by 100% as compared to a reference bacterial strain.

19. The isolated bacterial, fungal or yeast cell of claim 1, wherein the modification to yqhD gene comprises insertion, substitution, removal removing of nucleic acids in the yqhD gene or inactivation or knockout of the yqhD gene.

20. A method of growing a bacterial, fungal or yeast cell comprising culturing a bacterial, fungal or yeast cell according to claim 1 under conditions that allow for the growth of said bacterial, fungal or yeast cell.

21. A method for producing a desired product from a biomass, a hemicellulosic biomass, a lignocellulosic biomass, a cellulosic biomass or an oligosaccharide source comprising contacting the biomass, hemicellulosic biomass, lignocellulosic biomass, cellulosic biomass or oligosaccharide with the isolated bacterial, fungal or yeast cell according to claim 1 and producing said desired product by fermenting said biomass, a hemicellulosic biomass, a lignocellulosic biomass, a cellulosic biomass or an oligosaccharide source in the presence of said bacterial, fungal or yeast cell.

22. The method of claim 21, wherein the bacterial, fungal or yeast cell produces a desired product, or has been genetically engineered to produce a desired product, selected from the group consisting of ethanol, lactic acid, succinic acid, malic acid, acetic acid, 1,3-propanediol, 2,3-propanediol, 1,4-butanediol, 2,3-butanediol, butanol, pyruvate, dicarboxylic acids, adipic acid and amino acids.

\* \* \* \* \*

UNITED STATES PATENT AND TRADEMARK OFFICE
CERTIFICATE OF CORRECTION

Page 1 of 1

PATENT NO. : 9,157,102 B2
APPLICATION NO. : 14/008015
DATED : October 13, 2015
INVENTOR(S) : Elliot N. Miller et al.

It is certified that error appears in the above-identified patent and that said Letters Patent is hereby corrected as shown below:

Specification

Column 3,
Line 32, "50 g xylose," should read --50 g liter$^{-1}$ xylose,--.

Column 6,
Line 55, "a bacterial. fungal" should read --a bacterial, fungal--.

Claims

Column 49,
Lines 16-17, claim 13, "*Trametes Trametes versicolor*" should read
--*Trametes villosa, Trametes versicolor*--.

Signed and Sealed this
Twenty-ninth Day of March, 2016

Michelle K. Lee
*Director of the United States Patent and Trademark Office*

SEQUENCE LISTING

<160> NUMBER OF SEQ ID NOS: 32

<210> SEQ ID NO 1
<211> LENGTH: 382
<212> TYPE: PRT
<213> ORGANISM: Escherichia coli

<400> SEQUENCE: 1

Met Ala Asn Arg Met Ile Leu Asn Glu Thr Ala Trp Phe Gly Arg Gly
1               5                   10                  15

Ala Val Gly Ala Leu Thr Asp Glu Val Lys Arg Arg Gly Tyr Gln Lys
            20                  25                  30

Ala Leu Ile Val Thr Asp Lys Thr Leu Val Gln Cys Gly Val Val Ala
            35                  40                  45

Lys Val Thr Asp Lys Met Asp Ala Ala Gly Leu Ala Trp Ala Ile Tyr
 50                  55                  60

Asp Gly Val Val Pro Asn Pro Thr Ile Thr Val Lys Glu Gly Leu
 65                  70                  75                  80

Gly Val Phe Gln Asn Ser Gly Ala Asp Tyr Leu Ile Ala Ile Gly Gly
                85                  90                  95

Gly Ser Pro Gln Asp Thr Cys Lys Ala Ile Gly Ile Ile Ser Asn Asn
            100                 105                 110

Pro Glu Phe Ala Asp Val Arg Ser Leu Glu Gly Leu Ser Pro Thr Asn
            115                 120                 125

Lys Pro Ser Val Pro Ile Leu Ala Ile Pro Thr Thr Ala Gly Thr Ala
130                 135                 140

Ala Glu Val Thr Ile Asn Tyr Val Ile Thr Asp Glu Glu Lys Arg Arg
145                 150                 155                 160

Lys Phe Val Cys Val Asp Pro His Asp Ile Pro Gln Val Ala Phe Ile
                165                 170                 175

Asp Ala Asp Met Met Asp Gly Met Pro Pro Ala Leu Lys Ala Ala Thr
            180                 185                 190

Gly Val Asp Ala Leu Thr His Ala Ile Glu Gly Tyr Ile Thr Arg Gly
            195                 200                 205

Ala Trp Ala Leu Thr Asp Ala Leu His Ile Lys Ala Ile Glu Ile Ile
210                 215                 220

Ala Gly Ala Leu Arg Gly Ser Val Ala Gly Asp Lys Asp Ala Gly Glu
225                 230                 235                 240

Glu Met Ala Leu Gly Gln Tyr Val Ala Gly Met Gly Phe Ser Asn Val
                245                 250                 255

Gly Leu Gly Leu Val His Gly Met Ala His Pro Leu Gly Ala Phe Tyr
            260                 265                 270

Asn Thr Pro His Gly Val Ala Asn Ala Ile Leu Leu Pro His Val Met
            275                 280                 285

Arg Tyr Asn Ala Asp Phe Thr Gly Glu Lys Tyr Arg Asp Ile Ala Arg
290                 295                 300

Val Met Gly Val Lys Val Glu Gly Met Ser Leu Glu Glu Ala Arg Asn
305                 310                 315                 320

Ala Ala Val Glu Ala Val Phe Ala Leu Asn Arg Asp Val Gly Ile Pro
                325                 330                 335

Pro His Leu Arg Asp Val Gly Val Arg Lys Glu Asp Ile Pro Ala Leu
            340                 345                 350

Ala Gln Ala Ala Leu Asp Asp Val Cys Thr Gly Gly Asn Pro Arg Glu
            355                 360                 365

Ala Thr Leu Glu Asp Ile Val Glu Leu Tyr His Thr Ala Trp
370                 375                 380

<210> SEQ ID NO 2
<211> LENGTH: 1149
<212> TYPE: DNA
<213> ORGANISM: Escherichia coli

<400> SEQUENCE: 2
ttaccaggcg gtatggtaaa gctctacaat atcctcaagc gttgcttcac gcgggttgcc      60
accggtacaa acatcatcca gtgccgcctg agccagtgcc ggaatgtctt ccttgcgtac     120
accaacatca cgcaaatgtg gcggaatacc gacatcacgg ttgagagcaa acaccgcttc     180

```
aacagcggca ttacgcgcct cttccaggct catacctttcc actttcacgc ccataacgcg    240
cgcgatatcg cggtacttct caccggtaaa gtcagcgtta tagcgcatga catgcggtaa    300
caggatggcg ttcgcaacac cgtgtggagt gttgtaaaac gcgcccagtg gatgcgccat    360
accatgcacc aaccctaacc caacattcga gaagcccata cccgcaacat actgcccgag    420
cgccatttct tctccggcat ccttatcacc agcaaccgat cctcgcagcg ccccagcaat    480
gatttcaatc gctttaatgt gcagtgcatc ggttagcgcc cacgcgccac gggtaatata    540
cccctcaata gcatgagtga gcgcatcgac acccgtcgca gctttcagcg ctggaggcat    600
accatccatc atgtcagcgt caataaacgc cacctgcggg atatcatgcg gatcaacgca    660
aacaaacttg cgccgttttt cttcgtcagt gatcacgtag ttaatggtca cttctgccgc    720
agtgcctgct gtggtgggga ttgccagaat cggtacactg ggtttattgg tcggggaaag    780
tccttccagg ctacgcacat cggcaaactc cgggttgttg ctgataatgc caatcgcttt    840
acaagtatcc tgtggagaac caccaccaat agcgatcagg taatccgcgc cgctattctg    900
gaatacaccg agcccttctt tgacgacagt aattgttggg ttgggcacta cgccgtcgta    960
aatcgcccat gccagccctg cagcatccat cttatcggtc actttcgcca ccacgccgca   1020
ttgcaccagc gttttatcgg tgacgatcag cgccttctga taaccacggc gtttcacctc   1080
atcggttaaa gccccaacag caccccgacc aaaccatgcc gtttcgttca gaatcattct   1140
gttagccat                                                          1149
```

```
<210> SEQ ID NO 3
<211> LENGTH: 32
<212> TYPE: DNA
<213> ORGANISM: Artificial sequence
<220> FEATURE:
<223> OTHER INFORMATION: fucO for EcoRI primer

<400> SEQUENCE: 3
cgcgcggaat tcgattgccg tagtgctgga ga                                   32

<210> SEQ ID NO 4
<211> LENGTH: 32
<212> TYPE: DNA
<213> ORGANISM: Artificial sequence
<220> FEATURE:
<223> OTHER INFORMATION: fucO rev BamHI primer

<400> SEQUENCE: 4
cgcgcgggat cctgcggttg gtacggtaac gg                                   32

<210> SEQ ID NO 5
<211> LENGTH: 20
<212> TYPE: DNA
<213> ORGANISM: Artificial sequence
<220> FEATURE:
<223> OTHER INFORMATION: ldhA forward primer

<400> SEQUENCE: 5
gataacggag atcgggaatg                                                 20

<210> SEQ ID NO 6
<211> LENGTH: 20
<212> TYPE: DNA
<213> ORGANISM: Artificial sequence
<220> FEATURE:
<223> OTHER INFORMATION: ldhA reverse primer
```

<400> SEQUENCE: 6
ctttggctgt cagttcacca                                          20

<210> SEQ ID NO 7
<211> LENGTH: 20
<212> TYPE: DNA
<213> ORGANISM: Artificial sequence
<220> FEATURE:
<223> OTHER INFORMATION: ldha-1 primer

<400> SEQUENCE: 7
tctggaaaaa ggcgaaacct                                          20

<210> SEQ ID NO 8
<211> LENGTH: 21
<212> TYPE: DNA
<213> ORGANISM: Artificial sequence
<220> FEATURE:
<223> OTHER INFORMATION: ldha-2 primer

<400> SEQUENCE: 8
tttgtgctat aaacggcgag t                                        21

<210> SEQ ID NO 9
<211> LENGTH: 40
<212> TYPE: DNA
<213> ORGANISM: Artificial sequence
<220> FEATURE:
<223> OTHER INFORMATION: ldhL ORF up primer

<400> SEQUENCE: 9
atgtctaata ttcaaaatca tcaaaaagtt gtcctcgtcg                    40

<210> SEQ ID NO 10
<211> LENGTH: 35
<212> TYPE: DNA
<213> ORGANISM: Artificial sequence
<220> FEATURE:
<223> OTHER INFORMATION: ldhL ORF down primer

<400> SEQUENCE: 10
ttatttgtct tgttttcag caagagcgtt tagac                          35

<210> SEQ ID NO 11
<211> LENGTH: 28
<212> TYPE: DNA
<213> ORGANISM: Artificial sequence
<220> FEATURE:
<223> OTHER INFORMATION: ldhA reverse1 primer

<400> SEQUENCE: 11
aagactttct ccagtgatgt tgaatcac                                 28

<210> SEQ ID NO 12
<211> LENGTH: 15
<212> TYPE: DNA
<213> ORGANISM: Artificial sequence
<220> FEATURE:
<223> OTHER INFORMATION: ldhA forward1 primer

<400> SEQUENCE: 12
tcttgccgct cccct                                               15

```
<210> SEQ ID NO 13
<211> LENGTH: 20
<212> TYPE: DNA
<213> ORGANISM: Artificial sequence
<220> FEATURE:
<223> OTHER INFORMATION: pdc forward primer

<400> SEQUENCE: 13
tggtctcaag catcacttcg                                               20

<210> SEQ ID NO 14
<211> LENGTH: 20
<212> TYPE: DNA
<213> ORGANISM: Artificial sequence
<220> FEATURE:
<223> OTHER INFORMATION: adhB reverse primer

<400> SEQUENCE: 14
ttggtcagag cacaagcatc                                               20

<210> SEQ ID NO 15
<211> LENGTH: 20
<212> TYPE: DNA
<213> ORGANISM: Artificial sequence
<220> FEATURE:
<223> OTHER INFORMATION: adhB-1 primer

<400> SEQUENCE: 15
cccacgcatt tgaagcttat                                               20

<210> SEQ ID NO 16
<211> LENGTH: 20
<212> TYPE: DNA
<213> ORGANISM: Artificial sequence
<220> FEATURE:
<223> OTHER INFORMATION: pdc-2 primer

<400> SEQUENCE: 16
atcgatttta gccggagctt                                               20

<210> SEQ ID NO 17
<211> LENGTH: 20
<212> TYPE: DNA
<213> ORGANISM: Artificial sequence
<220> FEATURE:
<223> OTHER INFORMATION: estZ forward primer

<400> SEQUENCE: 17
actggcatct gagttctctg                                               20

<210> SEQ ID NO 18
<211> LENGTH: 20
<212> TYPE: DNA
<213> ORGANISM: Artificial sequence
<220> FEATURE:
<223> OTHER INFORMATION: estZ reverse primer

<400> SEQUENCE: 18
ttccatggcg tgagttactg                                               20

<210> SEQ ID NO 19
<211> LENGTH: 20
<212> TYPE: DNA
<213> ORGANISM: Artificial sequence
<220> FEATURE:
<223> OTHER INFORMATION: estZ-1 primer
```

```
<400> SEQUENCE: 19
cagaccgtgc ggaatatgga                                               20

<210> SEQ ID NO 20
<211> LENGTH: 20
<212> TYPE: DNA
<213> ORGANISM: Artificial sequence
<220> FEATURE:
<223> OTHER INFORMATION: estZ-2 primer

<400> SEQUENCE: 20
cagcctcgat tcgcatgaca                                               20

<210> SEQ ID NO 21
<211> LENGTH: 20
<212> TYPE: DNA
<213> ORGANISM: Artificial sequence
<220> FEATURE:
<223> OTHER INFORMATION: adhE forward primer

<400> SEQUENCE: 21
caatacgcct tttgacagca                                               20

<210> SEQ ID NO 22
<211> LENGTH: 20
<212> TYPE: DNA
<213> ORGANISM: Artificial sequence
<220> FEATURE:
<223> OTHER INFORMATION: adhE reverse primer

<400> SEQUENCE: 22
gccatcaatg gcaaaaagtt                                               20

<210> SEQ ID NO 23
<211> LENGTH: 19
<212> TYPE: DNA
<213> ORGANISM: Artificial sequence
<220> FEATURE:
<223> OTHER INFORMATION: adhE-1 primer

<400> SEQUENCE: 23
tcagtagcgc tgtctggca                                                19

<210> SEQ ID NO 24
<211> LENGTH: 34
<212> TYPE: DNA
<213> ORGANISM: Artificial sequence
<220> FEATURE:
<223> OTHER INFORMATION: adhE-2 primer

<400> SEQUENCE: 24
aatgctctcc tgataatgtt aaacttttttt agta                              34

<210> SEQ ID NO 25
<211> LENGTH: 20
<212> TYPE: DNA
<213> ORGANISM: Artificial sequence
<220> FEATURE:
<223> OTHER INFORMATION: yqhD forward primer

<400> SEQUENCE: 25
tatgatgcca ggctcgtaca                                               20
```

<210> SEQ ID NO 26
<211> LENGTH: 20
<212> TYPE: DNA
<213> ORGANISM: Artificial sequence
<220> FEATURE:
<223> OTHER INFORMATION: yqhD reverse primer

<400> SEQUENCE: 26
gatcatgcct ttccatgctt                                          20

<210> SEQ ID NO 27
<211> LENGTH: 24
<212> TYPE: DNA
<213> ORGANISM: Artificial sequence
<220> FEATURE:
<223> OTHER INFORMATION: yqhD-1 primer

<400> SEQUENCE: 27
gctttttacg cctcaaactt tcgt                                     24

<210> SEQ ID NO 28
<211> LENGTH: 19
<212> TYPE: DNA
<213> ORGANISM: Artificial sequence
<220> FEATURE:
<223> OTHER INFORMATION: yqhD-2 primer

<400> SEQUENCE: 28
tacttgctcc ctttgctgg                                           19

<210> SEQ ID NO 29
<211> LENGTH: 61
<212> TYPE: DNA
<213> ORGANISM: Artificial sequence
<220> FEATURE:
<223> OTHER INFORMATION: adhE-fucO ORF forward primer

<400> SEQUENCE: 29
aatgctctcc tgataatgtt aaactttttt agtaatgatg ctaacagaa tgattctgaa    60 c                                                              61

<210> SEQ ID NO 30
<211> LENGTH: 40
<212> TYPE: DNA
<213> ORGANISM: Artificial sequence
<220> FEATURE:
<223> OTHER INFORMATION: adhE-fucO ORF reverse primer

<400> SEQUENCE: 30
tgccagacag cgctactgat taccaggcgg tatggtaaag                     40

<210> SEQ ID NO 31
<211> LENGTH: 40
<212> TYPE: DNA
<213> ORGANISM: Artificial sequence
<220> FEATURE:
<223> OTHER INFORMATION: adhE-fucO-1 primer

<400> SEQUENCE: 31
ctttaccata ccgcctggta atcagtagcg ctgtctggca                     40

<210> SEQ ID NO 32
<211> LENGTH: 61
<212> TYPE: DNA
<213> ORGANISM: Artificial sequence

```
<220> FEATURE:
<223> OTHER INFORMATION: adhE-fucO-2 primer

<400> SEQUENCE: 32
gttcagaatc attctgttag ccatcattac taaaaaagtt taacattatc aggagagcat      60
t                                                                      61
```